US009938507B2

(12) United States Patent
Gern et al.

(10) Patent No.: US 9,938,507 B2
(45) Date of Patent: Apr. 10, 2018

(54) METHODS OF PROPAGATING RHINOVIRUS C IN PREVIOUSLY UNSUSCEPTIBLE CELL LINES

(71) Applicant: Wisconsin Alumni Research Foundation, Madison, WI (US)

(72) Inventors: James E. Gern, Madison, WI (US); Yury A. Bochkov, Fitchburg, WI (US); Ann C. Palmenberg, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/836,327

(22) Filed: Aug. 26, 2015

(65) Prior Publication Data

US 2017/0082609 A1 Mar. 23, 2017

Related U.S. Application Data

(60) Provisional application No. 62/043,517, filed on Aug. 29, 2014, provisional application No. 62/203,603, filed on Aug. 11, 2015.

(51) Int. Cl.

| | |
|---|---|
| *C12N 7/00* | (2006.01) |
| *G01N 33/50* | (2006.01) |
| *A61K 39/125* | (2006.01) |
| *C07K 14/005* | (2006.01) |
| *C07K 16/10* | (2006.01) |

(52) U.S. Cl.

CPC ........... *C12N 7/00* (2013.01); *G01N 33/5014* (2013.01); *C12N 2770/32751* (2013.01); *G01N 2333/095* (2013.01); *G01N 2500/10* (2013.01)

(58) Field of Classification Search

CPC ...................... C12N 7/00; C12N 15/86; C12N 2710/10343; A61K 39/12; C07K 14/005

See application file for complete search history.

(56) References Cited

PUBLICATIONS

Bonnelykke et al., "A genome-wide association study identifies CDHR3 as a susceptibility locus for early childhood asthma with severe exacerbations", Nature, 2014, 46(1):51-55.*

Ashraf, Shamaila, et al. "Biological characteristics and propagation of human rhinovirus-C in differentiated sinus epithelial cells." Virology 436 (2013) 143-149.

Basta, Holly A., et al. "Modeling of the human rhinovirus C capsid suggests possible causes for antiviral drug resistance." Virology 448 (2014) 82-90.

Basta, Holly A., et al. "Modeling of the human rhinovirus C capsid suggests a novel topography with insights on receptor preference and immunogenicity." Virology 448 (2014) 176-184.

Bizzintino, J., et al. "Association between human rhinovirus C and severity of acute asthma in children." European Respiratory Journal (2011) 37(5):1037-1042.

Bochkov, Yury A., et al. "Clinical and molecular features of human rhinovirus C." Microbes and Infection (2012) 14(6):485-494.

Bochkov, Yury A., et al. "Molecular Modeling, Organ Culture and Reverse Genetics for a Newly Identified Human Rhinovirus C." Nature Medicine (2011) 17(5):627-632.

Bønnelykke, Klaus, et al. "A genome-wide association study identifies CDHR3 as a susceptibility locus for early childhood asthma with severe exacerbations." Nature Genetics (2014) 46(1):51-55.

Cox, Desmond W., et al. "Human rhinovirus species C infection in young children with acute wheeze is associated with increased acute respiratory hospital admissions." American Journal of Respiratory and Critical Care Medicine (2013) 188(11):1358-1364.

Lee, Wai-Ming, et al. "A diverse group of previously unrecognized human rhinoviruses are common causes of respiratory illnesses in infants." PLoS ONE (2007) 2(10):e966.

Lee, Wai-Ming, et al."Human rhinovirus species and season of infection determine illness severity." American Journal of Respiratory and Critical Care Medicine (2012) 186(9):886-891.

McIntyre, Chloe L., et al. "Proposals for the classification of human rhinovirus species A, B and C into genotypically assigned types." Journal of General Virology (2013) 94(8):1791-1806.

Palmenberg, Ann C, et al. "Classification and evolution of human rhinoviruses." Method Mol. Bid. (2015) 1221:1-10.

* cited by examiner

*Primary Examiner* — Barry A Chestnut

(74) *Attorney, Agent, or Firm* — Quarles & Brady LLP

(57) ABSTRACT

The present invention provides methods of propagating rhinovirus C (RV-C) in a host cell; a host cell comprising an effective amount of a heterologous CDHR3 receptor such that the host cell can support propagation of rhinovirus C; and kits comprising at least one host cell previously unable to support rhinovirus C growth, wherein the host cell comprises a heterologous CDHR3 receptor and a sample of rhinovirus C. Methods of use are also provided.

7 Claims, 17 Drawing Sheets
(16 of 17 Drawing Sheet(s) Filed in Color)

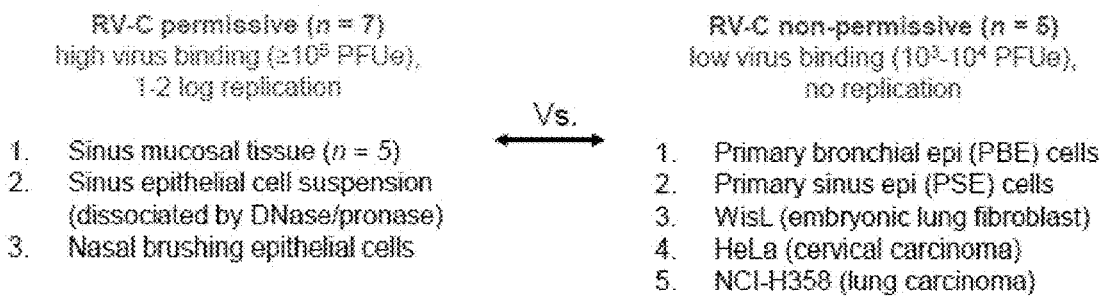
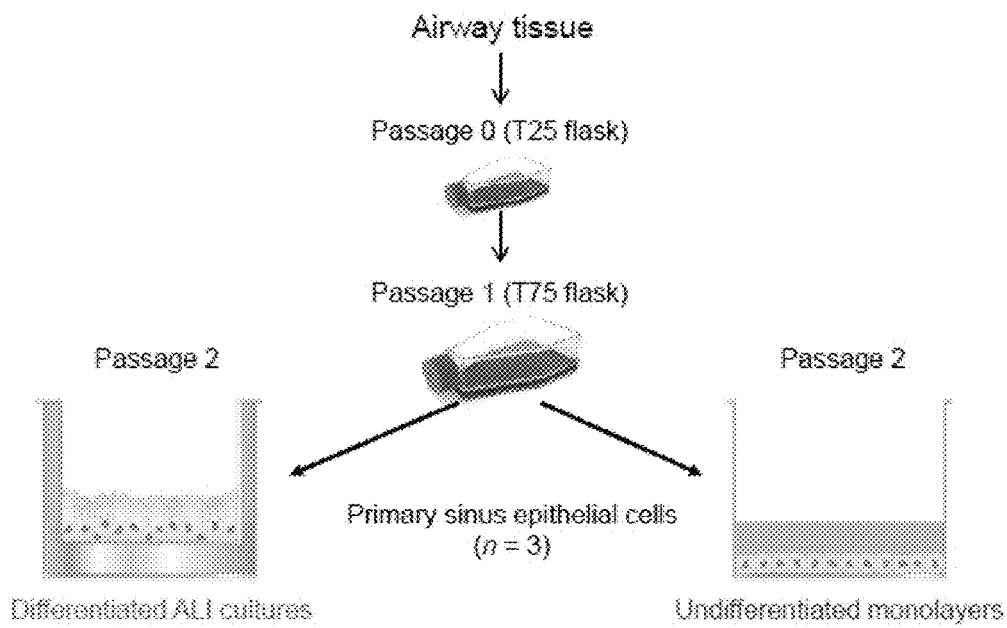
FIGURE 1

Experiment #1

Filtering steps:

Step 1. Adjusted $p$ <0.05, 8-fold upregulated in RV-C permissive cultures ($n$ = 415)

Step 2. Gene Ontology terms: membrane ($n$ = 100); plasma membrane ($n$ = 53); receptor ($n$ = 56).

Step 3. Expression level: RV-C permissive > 7 log2 > RV-C non-permissive membrane ($n$ = 40); plasma membrane ($n$ = 21); receptor ($n$ = 19).

Experiment #2

Filtering steps:

Step 1. Adjusted $p$ <0.05, 8-fold upregulated in RV-C permissive cultures ($n$ = 347)

Step 2. Gene Ontology terms: membrane ($n$ = 81); plasma membrane ($n$ = 38); receptor ($n$ = 32).

Step 3. Expression level: RV-C permissive > 7 log2 > RV-C non-permissive membrane ($n$ = 50); plasma membrane ($n$ = 28); receptor ($n$ = 18).

Experiment #1 and #2 - merged analysis

Filtering steps:

Step 1. Adjusted $p$ <0.05, 8-fold upregulated in RV-C permissive cultures ($n$ = 369)

Step 2. Gene Ontology terms: membrane ($n$ = 92); plasma membrane ($n$ = 50); receptor ($n$ = 43).

Step 3. Expression level: RV-C permissive > 7 log2 > RV-C non-permissive membrane ($n$ = 25); plasma membrane ($n$ = 11); receptor ($n$ = 11).

FIGURE 2

Step 1. Adjusted $p < 0.05$, 8-fold upregulated in RV-C permissive cultures;
(Exp.#1, $n = 415$; Exp.#2, $n = 347$).
Step 2. Gene Ontology terms: plasma membrane (Exp.#1, $n = 53$; Exp.#2, $n = 38$);
receptor (Exp.#1, $n = 56$; Exp.#2, $n = 32$);
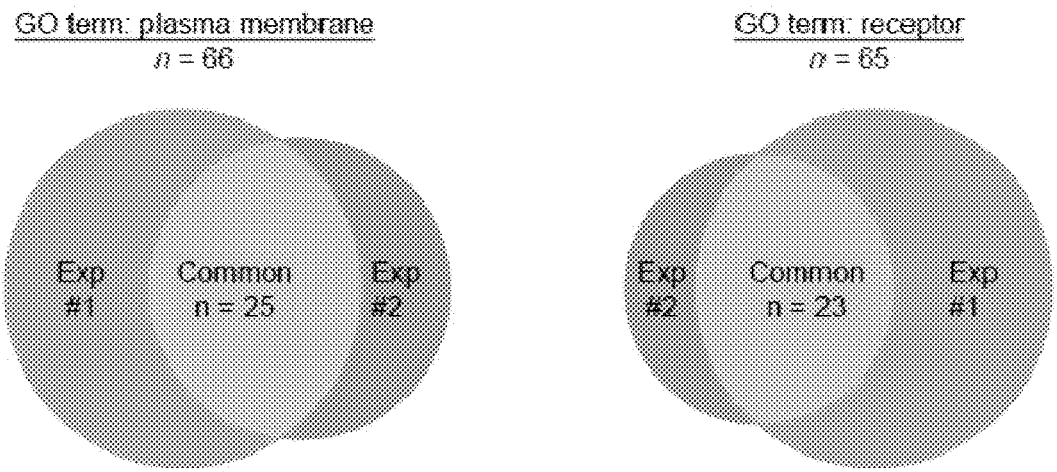
Step 3. Expression level: RV-C permissive > 7 log2 > RV-C non-permissive
plasma membrane (Exp.#1, $n = 21$; Exp.#2, $n = 28$)
receptor (Exp.#1, $n = 19$; Exp.#2, $n = 18$).
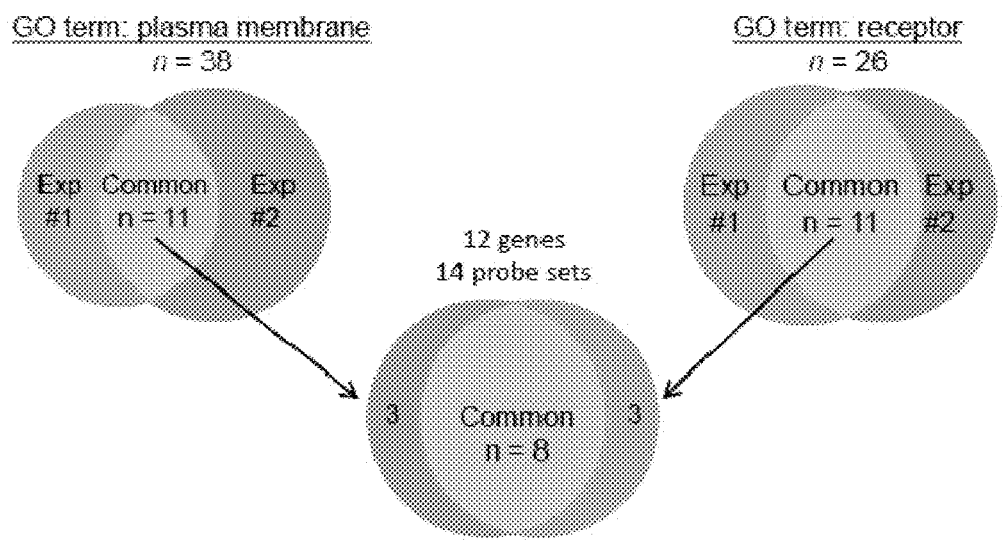
FIGURE 4

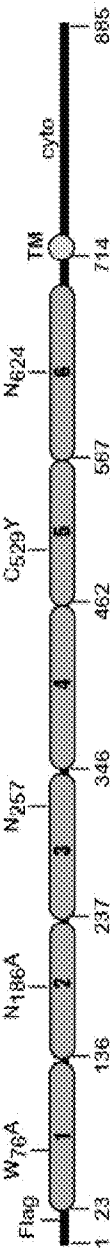
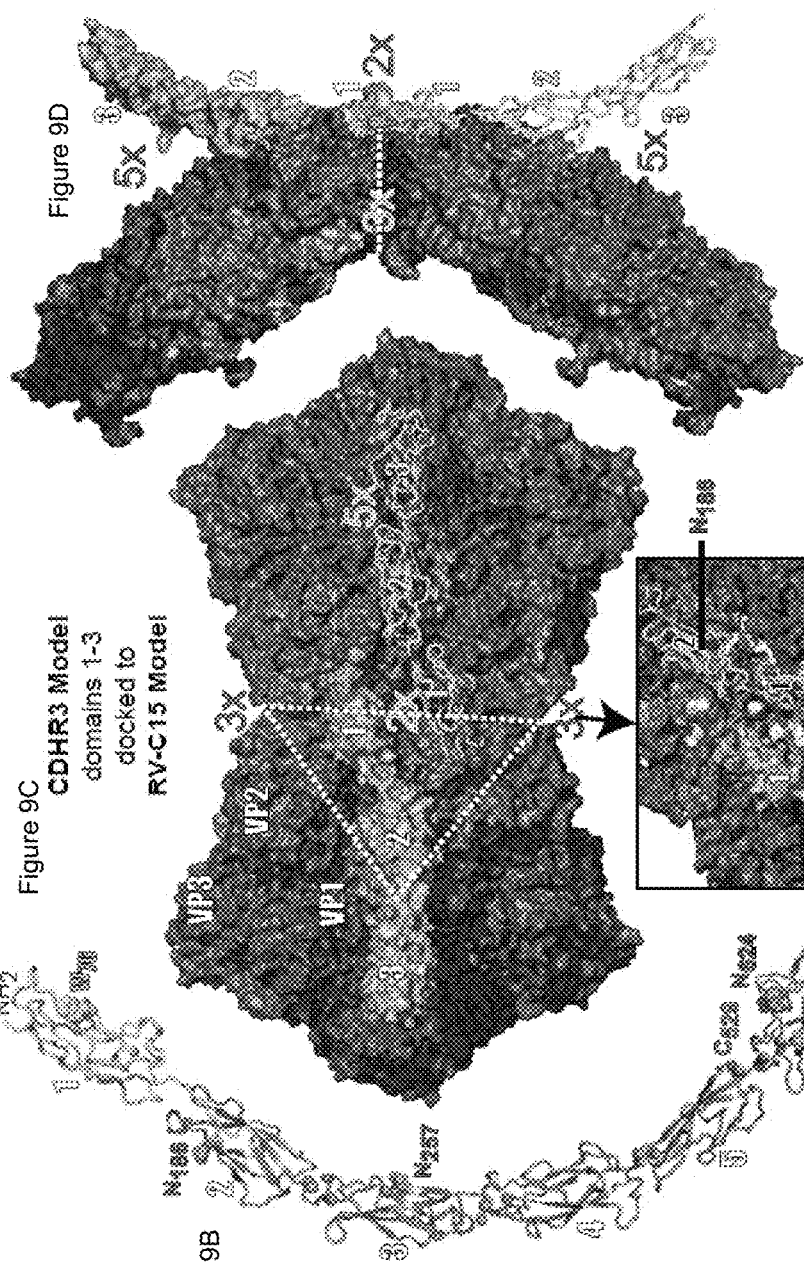
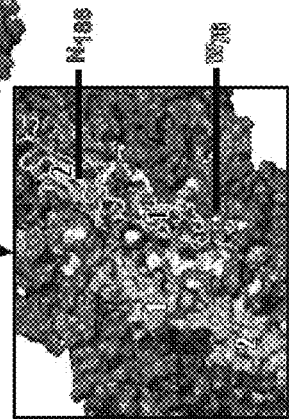
Figure 9A
Figure 9B
Figure 9C
Figure 9D
Figure 9E

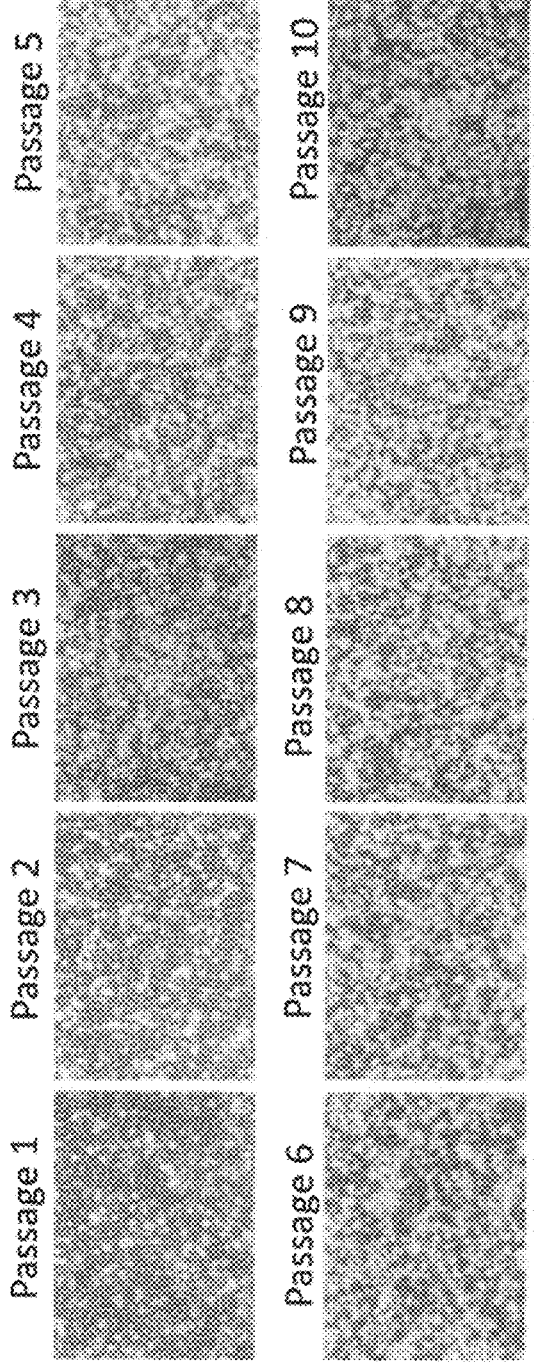
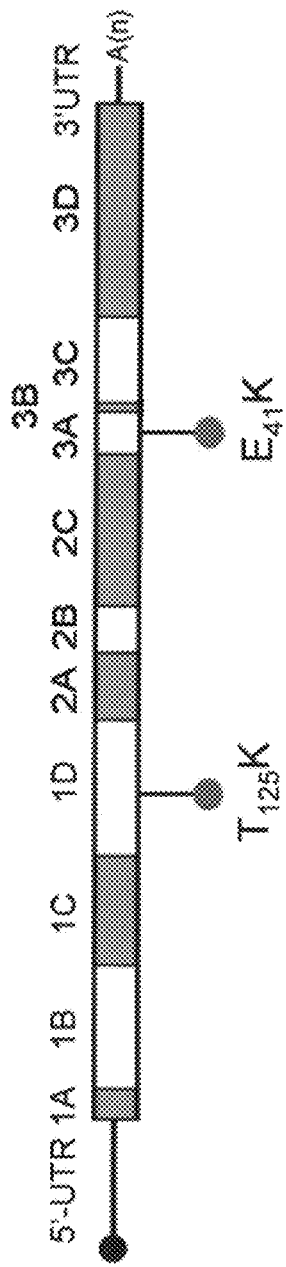
FIGURE 13

FIGURE 15

RV-C15-DsRed replication in HeLa-control cells 48h p.i.

| | GFP | DsRed | Phase contrast | Merged | pC15-DsRed wt
pC15-DsRed $K_{125}$
pC15-DsRed $K_{125}K_{41}$

FIGURE 17

SEQUENCE LISTING

```
<160> NUMBER OF SEQ ID NOS: 29

<210> SEQ ID NO 1
<211> LENGTH: 8
<212> TYPE: PRT
<213> ORGANISM: Artificial Sequence
<220> FEATURE:
<223> OTHER INFORMATION: Synthetic sequence

<400> SEQUENCE: 1

Asp Tyr Lys Asp Asp Asp Asp Lys
1               5

<210> SEQ ID NO 2
<211> LENGTH: 42
<212> TYPE: DNA
<213> ORGANISM: Artificial Sequence
<220> FEATURE:
<223> OTHER INFORMATION: Synthetic sequence

<400> SEQUENCE: 2
catcagctca gctggaccta gtgtgagcaa gggcgaggag ct                          42

<210> SEQ ID NO 3
<211> LENGTH: 42
<212> TYPE: DNA
<213> ORGANISM: Artificial Sequence
<220> FEATURE:
<223> OTHER INFORMATION: Synthetic sequence
```

<400> SEQUENCE: 3
gtcccgcaga actgatgagc ttgtacagct cgtccatgcc ga                              42

<210> SEQ ID NO 4
<211> LENGTH: 42
<212> TYPE: DNA
<213> ORGANISM: Artificial Sequence
<220> FEATURE:
<223> OTHER INFORMATION: Synthetic sequence

<400> SEQUENCE: 4
acaagctcat cagttctgcg ggaccgagcg acatgtttgt gc                              42

<210> SEQ ID NO 5
<211> LENGTH: 24
<212> TYPE: DNA
<213> ORGANISM: Artificial Sequence
<220> FEATURE:
<223> OTHER INFORMATION: Synthetic sequence

<400> SEQUENCE: 5
cctgcagtga tcataccaat caca                                                  24

<210> SEQ ID NO 6
<211> LENGTH: 32
<212> TYPE: DNA
<213> ORGANISM: Artificial Sequence
<220> FEATURE:
<223> OTHER INFORMATION: Synthetic sequence

<400> SEQUENCE: 6
atcactcgag atgatcatcg tggcgcatgt at                                         32

<210> SEQ ID NO 7
<211> LENGTH: 32
<212> TYPE: DNA
<213> ORGANISM: Artificial Sequence
<220> FEATURE:
<223> OTHER INFORMATION: Synthetic sequence

<400> SEQUENCE: 7
tgatcccggg tcaaaacaca gaatcctcca gg                                         32

<210> SEQ ID NO 8
<211> LENGTH: 30
<212> TYPE: DNA
<213> ORGANISM: Artificial Sequence
<220> FEATURE:
<223> OTHER INFORMATION: Synthetic sequence

<400> SEQUENCE: 8
atcactcgag atgaacaagg tcttcccccca                                           30

<210> SEQ ID NO 9
<211> LENGTH: 27
<212> TYPE: DNA
<213> ORGANISM: Artificial Sequence
<220> FEATURE:
<223> OTHER INFORMATION: Synthetic sequence

<400> SEQUENCE: 9
tgatcccggg tcagggtccg ggacagg                                               27

<210> SEQ ID NO 10

```
<211> LENGTH: 22
<212> TYPE: DNA
<213> ORGANISM: Artificial Sequence
<220> FEATURE:
<223> OTHER INFORMATION: Synthetic sequence

<400> SEQUENCE: 10
tcatcgtgga ggtgagggac ag                                              22

<210> SEQ ID NO 11
<211> LENGTH: 30
<212> TYPE: DNA
<213> ORGANISM: Artificial Sequence
<220> FEATURE:
<223> OTHER INFORMATION: Synthetic sequence

<400> SEQUENCE: 11
taaagtggac tatgaaacaa cccccatcta                                      30

<210> SEQ ID NO 12
<211> LENGTH: 30
<212> TYPE: DNA
<213> ORGANISM: Artificial Sequence
<220> FEATURE:
<223> OTHER INFORMATION: Synthetic sequence

<400> SEQUENCE: 12
tagatggggg ttgtttcata gtccacttta                                      30

<210> SEQ ID NO 13
<211> LENGTH: 20
<212> TYPE: DNA
<213> ORGANISM: Artificial Sequence
<220> FEATURE:
<223> OTHER INFORMATION: Synthetic sequence

<400> SEQUENCE: 13
cggcacgtac catgcagatg                                                 20

<210> SEQ ID NO 14
<211> LENGTH: 24
<212> TYPE: DNA
<213> ORGANISM: Artificial Sequence
<220> FEATURE:
<223> OTHER INFORMATION: Synthetic sequence

<400> SEQUENCE: 14
ccagtatctg ctccctgctt gtgt                                            24

<210> SEQ ID NO 15
<211> LENGTH: 55
<212> TYPE: DNA
<213> ORGANISM: Artificial Sequence
<220> FEATURE:
<223> OTHER INFORMATION: Synthetic sequence

<400> SEQUENCE: 15
gattaggtgt agcttatcgt cgtcatcctt gtaatctgct tctcccctg acatg           55

<210> SEQ ID NO 16
<211> LENGTH: 57
<212> TYPE: DNA
<213> ORGANISM: Artificial Sequence
<220> FEATURE:
<223> OTHER INFORMATION: Synthetic sequence

<400> SEQUENCE: 16
```
gagaagcaga ttacaaggat gacgacgata agctacacct aatcctctta cctgcta    57

<210> SEQ ID NO 17
<211> LENGTH: 25
<212> TYPE: DNA
<213> ORGANISM: Artificial Sequence
<220> FEATURE:
<223> OTHER INFORMATION: Synthetic sequence

<400> SEQUENCE: 17
ggactcagtt cctccaggac tgtgt    25

<210> SEQ ID NO 18
<211> LENGTH: 33
<212> TYPE: DNA
<213> ORGANISM: Artificial Sequence
<220> FEATURE:
<223> OTHER INFORMATION: Synthetic sequence

<400> SEQUENCE: 18
gcttttaggg tgaatgcgct gtcaggcacc tac    33

<210> SEQ ID NO 19
<211> LENGTH: 33
<212> TYPE: DNA
<213> ORGANISM: Artificial Sequence
<220> FEATURE:
<223> OTHER INFORMATION: Synthetic sequence

<400> SEQUENCE: 19
gtaggtgcct gacagcgcat tcaccctaaa agc    33

<210> SEQ ID NO 20
<211> LENGTH: 30
<212> TYPE: DNA
<213> ORGANISM: Artificial Sequence
<220> FEATURE:
<223> OTHER INFORMATION: Synthetic sequence

<400> SEQUENCE: 20
cagaatgtct gctgctggca ccctcttctc    30

<210> SEQ ID NO 21
<211> LENGTH: 30
<212> TYPE: DNA
<213> ORGANISM: Artificial Sequence
<220> FEATURE:
<223> OTHER INFORMATION: Synthetic sequence

<400> SEQUENCE: 21
gagaagaggg tgccagcagc agacattctg    30

<210> SEQ ID NO 22
<211> LENGTH: 30
<212> TYPE: DNA
<213> ORGANISM: Artificial Sequence
<220> FEATURE:
<223> OTHER INFORMATION: Synthetic sequence

<400> SEQUENCE: 22
cagaatgtct gctcaaggca ccctcttctc    30

<210> SEQ ID NO 23
<211> LENGTH: 30
<212> TYPE: DNA

<213> ORGANISM: Artificial Sequence
<220> FEATURE:
<223> OTHER INFORMATION: Synthetic sequence

<400> SEQUENCE: 23
gagaagaggg tgccttgagc agacattctg                                          30

<210> SEQ ID NO 24
<211> LENGTH: 32
<212> TYPE: DNA
<213> ORGANISM: Artificial Sequence
<220> FEATURE:
<223> OTHER INFORMATION: Synthetic sequence

<400> SEQUENCE: 24
tagaggtgga ggggatttga gttgactatc tg                                       32

<210> SEQ ID NO 25
<211> LENGTH: 36
<212> TYPE: DNA
<213> ORGANISM: Artificial Sequence
<220> FEATURE:
<223> OTHER INFORMATION: Synthetic sequence

<400> SEQUENCE: 25
atcccctcca cctctacata gtagaaagag caaacc                                   36

<210> SEQ ID NO 26
<211> LENGTH: 44
<212> TYPE: DNA
<213> ORGANISM: Artificial Sequence
<220> FEATURE:
<223> OTHER INFORMATION: Synthetic sequence

<400> SEQUENCE: 26
tcgttgaggt gtagaccttc tgccaagttg ccttgaaact gagg                          44

<210> SEQ ID NO 27
<211> LENGTH: 42
<212> TYPE: DNA
<213> ORGANISM: Artificial Sequence
<220> FEATURE:
<223> OTHER INFORMATION: Synthetic sequence

<400> SEQUENCE: 27
tctacacctc aacgacgaag tccctcgctt taccagcccg ac                            42

<210> SEQ ID NO 28
<211> LENGTH: 20
<212> TYPE: DNA
<213> ORGANISM: Artificial Sequence
<220> FEATURE:
<223> OTHER INFORMATION: Synthetic sequence

<400> SEQUENCE: 28
gtaggcgtgt acggtgggag                                                     20

<210> SEQ ID NO 29
<211> LENGTH: 25
<212> TYPE: DNA
<213> ORGANISM: Artificial Sequence

```
<220> FEATURE:
<223> OTHER INFORMATION: Synthetic sequence

<400> SEQUENCE: 29
ctccaggact gtgtacactc gtgtc                                              25
```

METHODS OF PROPAGATING RHINOVIRUS C IN PREVIOUSLY UNSUSCEPTIBLE CELL LINES

CROSS-REFERENCE TO RELATED APPLICATIONS

This application claims the benefit of U.S. Provisional Patent Application 62/043,517, filed Aug. 29, 2014, and U.S. Provisional Patent Application 62/203,603, filed Aug. 11, 2015.

STATEMENT REGARDING FEDERALLY SPONSORED RESEARCH OR DEVELOPMENT

This invention was made with government support under AI104317 awarded by the National Institutes of Health. The government has certain rights in the invention.

SEQUENCE LISTING STATEMENT

The application includes the sequence listing that is concurrently filed in computer readable form. This sequence listing is incorporated by reference herein.

FIELD OF THE INVENTION

This invention relates generally to the production of rhinoviruses, specifically to methods of propagating rhinovirus C (RV-C).

BACKGROUND

More than 160 types of rhinoviruses (RVs) are known. RVs are currently classified into three species (A, B and C) of Enteroviruses in the family Picornaviridae. RV-A and RV-B have been known for many years, but the discovery of RV-C in 2006 surprised the molecular and clinical virology communities.

The RV-C are clearly rhinoviruses, but unlike RV-A or RV-B, they are not readily propagated in typical cell culture systems. For example, conventional cells lines such as NCI-H358, WI-38, WisL, HEK293T, BEAS-2B, A549 and HeLa, do not support any detectable RV-C replication. The RV-C are not "new" in terms of evolution, but rather they were physically undetected by typical characterization methods that required cultured virus growth and induction of cytopathic effects, such as endpoint dilution ($TCID_{50}$) or plaque assays.

The current 55 recognized RV-C types (as determined by sequence analysis) were instead identified by PCR and sequencing while fishing through patient samples for other RV. As with the RV-A and B, each RV-C type includes those isolates whose VP1 sequences exceed 87% pair-wise identity at the nucleotide level. RV-C types have special clinical relevance since it is now recognized these strains are associated with up to half of rhinovirus illnesses in young children. They infect and replicate in both the lower and upper airways and tolerate higher growth temperatures in culture. Moreover, the RV-C use cell receptors that are not common to RV-A or RV-B.

Unfortunately, these receptors are apparently lost whenever primary airway mucosal tissue snippets are transitioned to undifferentiated monolayers since only fully differentiated cultures support RV-C replication in vitro. Small amounts of RV-C can be grown in mucosal organ cultures, but this technique requires the availability of primary human donor samples. Parallel work with differentiated sinus or bronchial epithelial cells cultured at air-liquid interface (ALI) is promising, but neither technique can produce enough RV-C for extensive biological studies.

Multiple attempts to grow RV-C in established cell lines have been unsuccessful. Relatively small quantities of RV-C can be produced using reverse genetics, as the full-length viral RNA transcripts synthesized in vitro are infectious when transfected into human cell lines (including, for example, the NCI-H358, WI-38, WisL, HEK293T, BEAS-2B, A549 and HeLa cell lines) which are normally not permissive to direct viral infection.

However, existing RV-C culture systems have relatively low throughput of virus and are labor intensive compared to those for other RVs. Failure to identify the cellular receptor and the inability to propagate RV-C in convenient cell lines has been a major obstacle to the study of virus-specific characteristics that could lead to effective antiviral strategies for this common and important respiratory pathogen.

Therefore, a need exists for methods of growing RV-C in a manner that provides large quantities of virus in an efficient, cost-effective way. Further, a need exists for methods of propagating RV-C using established cell lines.

BRIEF SUMMARY OF THE INVENTION

The present invention provides a method of propagating RV-C. In one embodiment, the method comprises obtaining a host cell expressing at least one heterologous CDHR3 receptor and infecting the host cell with a sample of RV-C or a RV-C variant, wherein the RV-C or RV-C variant propagates.

In one embodiment, the CDHR3 receptor is the wild-type CDHR3. In another embodiment, the CDHR3 receptor is the $CDHR3-C_{529}Y$ variant.

In one embodiment, the host cell is any cell capable of supporting RV-C replication. In one embodiment, the host cell has been previously unable to support RV-C replication, such as, for example, cell lines including NCI-H358, WI-38, WisL, HEK293T, BEAS-2B, A549 and HeLa and the like.

In one embodiment, the CDHR3 receptor is over-expressed in a suitable host cell, preferably via transduction with replication-deficient lentiviral particles produced using viral expression vectors known to the art, such as, for example, the viral vectors pDuet011, pNG72, pLX304, and the like. In other embodiments, the CDHR3 receptor expression is accomplished by transfection with a plasmid vector such as pTCN (TransOmic) expressing CDHR3 under control of CMV promoter.

In one embodiment, the transduced cells (~$10^7$ cells) yield a viral titer of at least greater than $10^8$ PFU equivalents or show a 1-log (ten-fold) increase over input virus.

The present invention also provides a kit comprising at least one host cell, wherein the host cell comprises a heterologous CDHR3 receptor and a control sample of RV-C or RV-C variant.

In another embodiment, the present invention provides a kit comprising a nucleic acid encoding a CDHR3 receptor and a control sample of RV-C or RV-C variant.

The present invention also provides a host cell infected with RV-C or RV-C variant, wherein the host cell has been modified to express an effective amount of a CDHR3 receptor such that the host cell can support propagation of RV-C.

In another embodiment, the present invention is a method of screening for a RV-C inhibitor comprising the step of examining the efficacy of proposed inhibitors on the interaction between RV-C or an RV-C variant and a host cell, wherein the host cell has been modified to express an effective amount of a CDHR3 receptor such that the host cell can support propagation of RV-C or RV-C variant.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1 depicts a set of experiments involving RV-C infection permissive versus non-permissive cultures. Monolayers of primary airway epithelial cells (nasal and bronchial), and transformed cell lines were cultured submerged in 12-well plates. Differentiated sinus epithelial cells were cultured at an air-liquid interface (ALI). Residual airway tissue specimens obtained after endoscopic sinus surgery were washed, sectioned and cultured submerged. Total RNA samples were extracted from cultured cells and mucosal tissue specimens, treated with RQ1 DNase, labeled, fragmented and hybridized to Human Gene 1.0 ST arrays (Affymetrix).

FIG. 2 is a gene expression analysis workflow. Raw data (.cel files) were uploaded into ArrayStar™ software version 4.0 (DNASTAR Inc., Madison, Wis.) for normalization and statistical analysis. The robust multichip analysis (RMA) algorithm was used for background correction, quantile normalization and median polish summarization. The differentially expressed genes were initially filtered on the basis of >8-fold up-regulation in RV-C permissive cultures at 95% confidence level (Student's t-test, Benjamin-Hotchberg multiple testing correction). Next, the genes with known or predicted membrane localization or receptor activity were selected. Finally, the selected genes were filtered using the expression level criteria (RV-C permissive>7 log 2>RV-C non-permissive).

FIG. 4 is a series of Venn diagrams showing the common receptor candidate genes identified in two microarray experiments after the filtering steps. The differentially expressed genes were filtered stepwise on the basis of the indicated criteria and the diagrams were generated by ArrayStar™ software version 4.0 (DNASTAR Inc., Madison, Wis.).

FIG. 9A illustrates a structure modeling of RV-C15 binding to CDHR3, specifically, a schematic map of the CDHR3 protein with indicated domains and point mutations.

FIG. 9B illustrates a structure modeling of RV-C15 binding to CDHR3, specifically, a structural model of the complete CDHR3 protein. Domain 1 was added to the published model of domains 2-6 (ref 19) after I-Tasser modeling relative to known cadherin structures. Key residues are highlighted. Gray spheres are interdomain calcium ions from PDB: 3Q2W.

FIG. 9C illustrates a structure modeling of RV-C15 binding to CDHR3, specifically, a surface model of domains 1-3 docked to two RV-C15 protomers (model), projected onto pentamer coordinates. VP1 (blue), VP2 (green) and VP3 (red), are shown following standard colors. Model was then duplicated across 2-fold axis to show putative paired orientations. Triangle marks icosahedral subunit. Biological subunit would include clockwise VP3.

FIG. 9D illustrates a structure modeling of RV-C15 binding to CDHR3, specifically, the same as C, rotated x=90°, y=90°.

FIG. 9E illustrates a structure modeling of RV-C15 binding to CDHR3, specifically, it is similar to FIG. 9C with highlights (white) showing all RV-C15 surface amino acid residues conserved with >90% identity among all known RV-C isolates.

FIG. 13 demonstrates serial passaging of RV-C15 in HeLa-E8 cells. Microphotographs (72 h p.i.) show progression of cytopathic effects from passage 1 to passage 10 in infected HeLa-E8 cells. Key mutations responsible for HeLa-adapted virus phenotype are mapped to viral genome schematic.

FIG. 15 graphs RV-C15-DsRed reporter cDNA clones

FIG. 17 shows RV-C15-DsRed replication in HeLa-control cells. Fluorescent microscopy imaging of control HeLa cells infected with RV-C15 reporter viruses for 48 h.

DETAILED DESCRIPTION OF THE INVENTION

In General. Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The Invention. In one embodiment, the present invention provides a method of propagating RV-C. In one embodiment, the method comprises obtaining a host cell expressing at least one heterologous CDHR3 receptor and infecting the host cell with a sample of RV-C, wherein the RV-C propagates.

By "propagating" we mean causing RV-C to multiply or increase in amount at least 10-fold compared to input virus.

Figure 12:
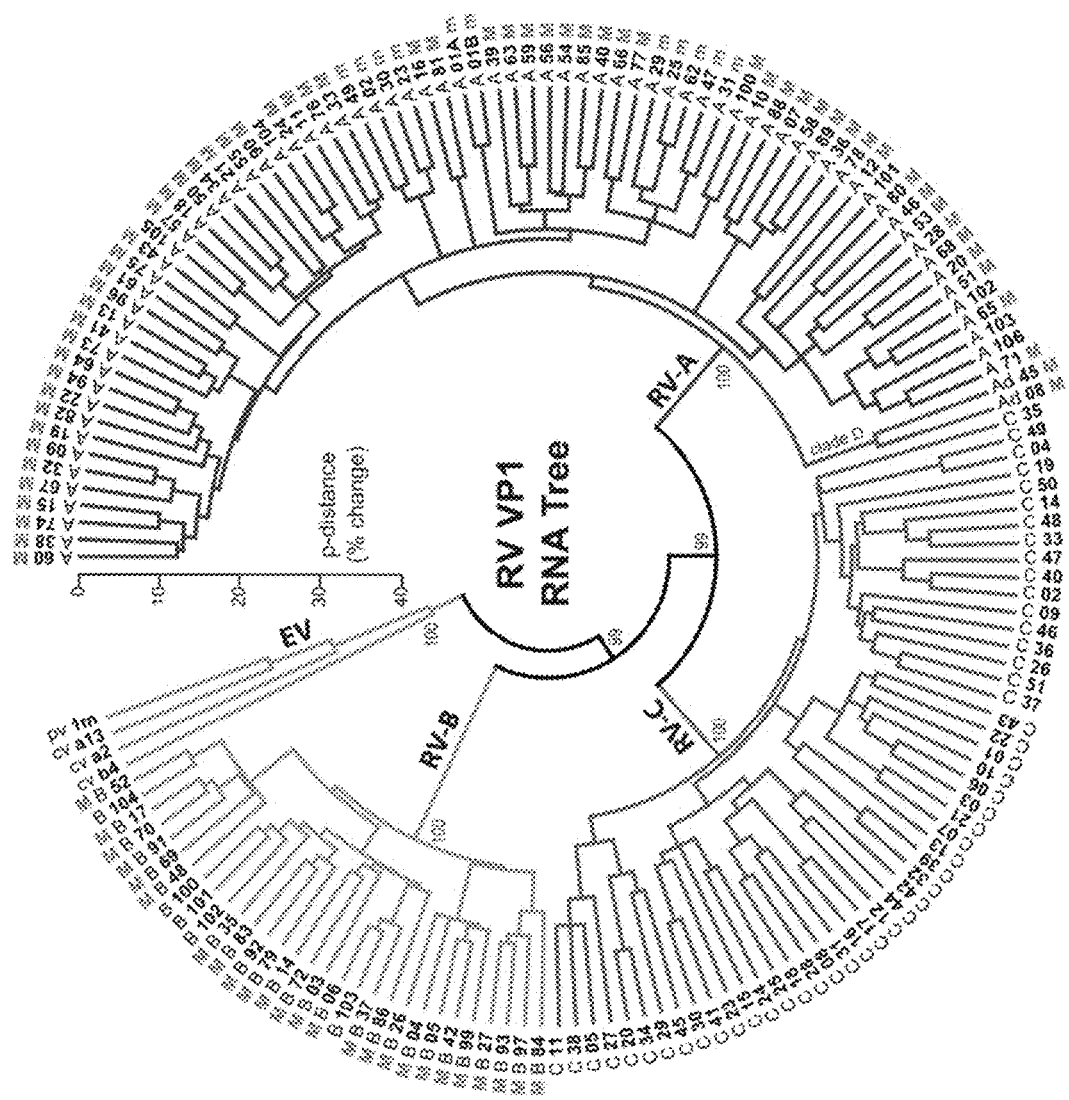
FIG. 12 a Circle phylogram of relationships for currently recognized genotypes (8) of RV-A, RV-B and RV-C. The tree was calculated with neighbor joining methods from aligned, VP1 RNA sequences, and rooted with data from four enteroviruses (EV) of the EV-A, EV-B and EV-C species. The Major ("M", ICAM-1) and minor ("m", LDLR) receptor groups are indicated if determined experimentally. The RV-C receptor is unknown. Bootstrap values (percent of 200 replicates) are indicated at key nodes.

By "rhinovirus C (RV-C)" we mean a strain of RV-C, preferably one known to the art (see McIntyre, J of Gen. Virology, 2013, 94, 1791-1806). In particular, we mean a strain of RV-C as shown in FIG. 12, including, for example and without limitation, strains RV-C15, RV-C2 and RV-C41.

By "RV-C variant", we mean a RV-C strain that has been modified, either naturally or by molecular biological methods.

By "host cell" we mean a cell capable of supporting RV-C or RV-C variant replication. In one embodiment, the host cell is a cell that was previously unable to support RV-C replication, such as, for example, cells like NCI-H358, WI-38, WisL, HEK293T, BEAS-2B, A549 and HeLa. A preferred suitable host cell is also a cell that can be cultured, preferably in a large-scale production method such as suspension culture. In addition, a preferred suitable host cell is capable of the uniform expression of heterologous CDHR3, and able to support passaging the cells at least 10 times in tissue culture. Both of these characteristics will differentiate the CDHR3-expressing cell line from primary cells.

In one embodiment, the method comprises obtaining a host cell comprising at least one heterologous CDHR3 receptor and infecting the host cell with a sample of RV-C, wherein the RV-C propagates.

By "CDHR3 receptor" we mean human cadherin-related family member 3. CDHR3 is a member of the cadherin family of transmembrane proteins with an as yet unknown biological function that is highly expressed in human lung tissue, bronchial epithelium and during mucociliary differentiation in human airway epithelial cells. Members of the cadherin family are responsible for communication between identical cells through calcium-dependent interactions. Cadherins on the same cell surface can self-associate into cis-dimers (lateral dimers) while cell adhesion is based on interactions between identical cadherins on neighboring cell surfaces to form trans-dimers. Our structure modeling of the CDHR3-virus complex identified a potential binding site for monomers and dimers in a region of the RV-C15 capsid that is highly conserved among different RV-C types.

In one embodiment, the CDHR3 receptor is the wild-type receptor, while in other embodiments the receptor is the CDHR3-$C_{529}Y$ variant encoded by the rs6967330 SNP. (See Bonnelykke, K. et al. Nat. Genet., 2014, 46, 51-55). In our studies that gave rise to the present invention, cells transfected with the CDHR3-$C_{529}Y$ variant had about a 10-fold increase in RV-C binding and progeny yields compared to wild-type CDHR3. Modeling of CDHR3 structure identified potential binding sites that could impact the virus surface in regions which are highly conserved among all RV-C types. Notably, our findings demonstrate that a coding SNP (rs6967330) in CDHR3 previously associated with wheezing illnesses and hospitalizations in childhood asthma (by genetic analysis) is also associated with increased RV-C binding and replication in vitro. These findings suggest that the rs6967330 SNP promotes RV-C wheezing illnesses in infancy, which adversely affects the developing lung to increase the risk of asthma.

In one embodiment, the host cell is transfected with nucleic acids encoding at least one CDHR3 receptor. By "transfected" we mean any means of deliberately introducing nucleic acids into a cell. In one embodiment, the CDHR3 receptor is transduced into the host cell by a viral vector. By "viral vector" we mean any virus (such as retrovirus or adenovirus) known to the art that is capable of delivering genetic material (CDHR3 receptor sequence under control of a viral promoter) into cells, including but not limited to retroviral expression vectors pDuet011, pNG72, pLX304 used for production of pseudovirus particles. In one embodiment, the viral vector yields a viral titer of at least a 10-fold increase over input virus.

The present invention also provides a host cell infected with RV-C, wherein the host cell has been modified to express an effective amount of a heterologous CDHR3 receptor such that the host cell can support propagation of RV-C. By "effective amount" we mean an amount of CDHR3 receptor effective to achieve the desired result, such as the propagation of RV-C yielding at least a ten-fold increase in virus progeny over input virus.

Methods of Use. The present invention provides important tools that can be used to cure the common cold, define RV-C molecular virology, study mechanisms of virus growth, screen for antivirals, culture new isolates of RV-C, measure RV-C infectivity, and evaluate immunological status of patients to engage in clinical and antiviral research. The cure for the common cold has been elusive, in part due to incomplete information on the molecular biology of RV-C, an important cause of both upper and lower respiratory illness.

The present invention will allow the high-throughput large-scale propagation of RV-C. Expression of CDHR3 in cell lines suitable for high-throughput large-scale propagation of RV-C by infection enables production of large quantities of virus that can be used to determine the actual, rather than modeled, virion crystal structure, and in the development of RV-C vaccines.

By "high-throughput large-scale propagation" we mean any method of automating experiments such that large scale repetition becomes feasible.

In addition, the methods of the present invention can be used as RV-C infectivity assays for antiviral drug screening. No vaccines or effective anti-virals are currently available for RV-C. Blocking interactions between major receptor group RVs and ICAM-1 inhibits infection, airway inflammation and illness but is ineffective against replication of minor receptor group viruses or RV-C types. Anti-CDHR3 antibodies, soluble CDHR3 or short peptides specifically targeting virus-binding sites could serve as inhibitors of RV-C infection and provide a new therapeutic approach for RV-C induced illnesses. Development of RV-C specific antiviral drugs may be especially important for treatment of infants and children with the rs6967330 asthma risk allele in CDHR3.

As an example of examining an anti-viral candidate, equivalent samples of an RV-C virus can be treated (or not, in the case of a control) with a putative anti-RV drug. The samples are then inoculated onto CDHR3-expressing cells. After 24-48 hrs, the comparative levels of virus growth can be measured as an indicator of drug effectiveness. Inhibitory effects on virus growth relative to the control sample would indicate an active compound.

With the CDHR3-expressing cells and HeLa-adapted virus, comparative virus growth can (now) be readily quantitated by standard plaque assay or real-time PCR techniques as have been described for other Enterovirus drug screening protocols. Pleconaril inhibition of RV-A and RV-B was previously documented in similar assays using unmodified HeLa cells.

In another example, putative anti-RV drugs ("test compounds") could be added to the CDHR3-expressing cells before RV-C infection, and again, the corresponding reduction (or not) in subsequent virus growth in those cells is monitored. Rupintrivir inhibition of RV-A and RV-B was previously documented by this technique using unmodified HeLa cells. Either type of drug addition protocol (pre or post infection) can easily be scaled for high throughput, but only in a system that uses cells capable of growing high-titer RV-C, i.e. the current invention.

The present invention also provides methods of detecting a neutralizing antibody response to RV-C in clinical studies.

Kits. In another embodiment, the present invention provides a kit comprising at least one host cell previously unsusceptible to RV-C infection, wherein the host cell comprises an effective amount of a heterologous CDHR3 receptor; and a control sample of RV-C or RV-C variant.

In another embodiment, the kit comprises a transduced, clonally selected cell line stably expressing the CDHR3-$C_{529}Y$ variant; lentiviral particles for cell transduction; and lentiviral CDHR3-expressing vectors for production of these particles or any plasmid expressing CDHR3 under control of a promoter (e.g. cytomegalovirus (CMV) and simian virus 40 (SV40)) for transfection. In addition to stably expressing cells or lentiviral vector for CDHR3 expression, in an alternate embodiment of the invention, the kit comprises viral particles ready for transduction of any cell line of interest. In one embodiment, the CDHR3 may be transduced into the host cell by infection with viral particles produced using a viral vector.

In yet another embodiment, the kit comprises a viral vector for producing viral particles capable of transducing a host cell with the CDHR3 receptor sequence; and a sample of RV-C. The kit may also comprise a vector enabling a CDHR3 receptor expression and a control sample of RV-C.

Instructional material may also be included in the kits of the present invention. By "instructional material" we mean a publication, a recording, a diagram, or any other medium of expression which is used to communicate the usefulness of the invention.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed description of the novel methods, cell and kits of the present invention are to be regarded as illustrative in nature and not restrictive.

EXAMPLES

The following examples are, of course, offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

Example 1

In Silico Identification of the RV-C Receptor

To obtain a working list of potential cellular receptors, we measured gene expression on array chips (Human Gene 1.0 ST Array, Affymetrix) in two series of experiments involving cells that were either susceptible or not susceptible to RV-C infection (FIG. 1). In one experimental series, susceptible cells included whole sinus mucosal tissue specimens (n=5), epithelial cell suspension from sinus tissue, and nasal epithelium obtained via brushing, while non-susceptible cells included monolayers of primary undifferentiated epithelial cells and transformed cell lines (n=5, including HeLa). In a second experimental series, we compared three pairs of undifferentiated and fully differentiated (ALI) sinus epithelial cell cultures.

By in silico analysis of expression profiles, we identified a total of 415 and 347 genes, preferentially expressed (>8-fold difference, adjusted P<0.05) in virus-susceptible cells in the first and second experiments, respectively. We then performed additional filtering steps to narrow the candidate gene lists on the basis of available Gene Ontology information (membrane localization, receptor activity) and expression levels of the known rhinovirus receptor genes (FIG. 2 and Table 1).

Figure 3:
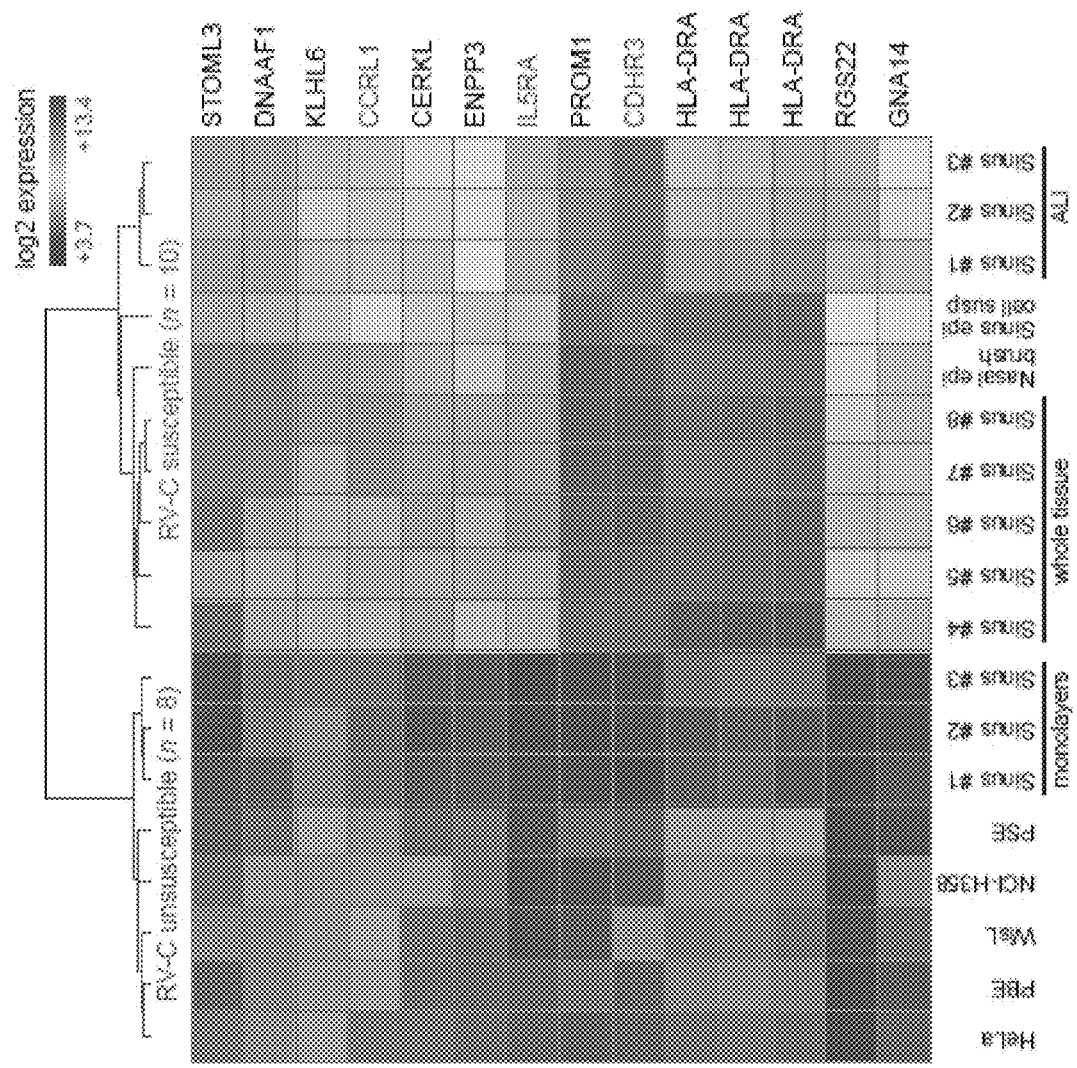
FIG. 3 is a heat map showing clustering analysis of gene expression patterns in cells susceptible or unsusceptible to RV-C infection. Candidate genes selected for validation of RV-C receptor activity are shown in red. Expression intensity values were analyzed by hierarchical clustering of samples and genes using the Euclidean distance metric with centroid linkage method using ArrayStar™ software version 4.0 (DNASTAR Inc., Madison, Wis.). Color bar represents gene expression intensity (log 2 scale).

We identified a total of 12 common genes (represented by 14 probe sets) encoding proteins localized to plasma membrane, and/or with predicted or functionally demonstrated receptor activity, including members of the Human MHC class II, stomatin, guanine nucleotide-binding, type I cytokine and atypical chemokine receptor and cadherin protein families (FIG. 3 and FIG. 4).

Figure 5:
FIG. 5 is a heat map showing clustering analysis of gene expression patterns in cell cultures. The differentially expressed genes were selected on the basis of (i) >8-fold upregulation in RV-C susceptible cultures at 95% confidence level (Student's t-test, Benjamini-Hotchberg multiple testing correction), (ii) known or predicted membrane localization and (iii) the expression level criteria (RV-C permissive>7 log 2>RV-C non-permissive). Candidate genes selected for validation of RV-C receptor activity are shown in red. Expression intensity values were analyzed by hierarchical clustering of samples and genes using the Euclidean distance metric with centroid linkage method using ArrayStar™ software version 4.0 (DNASTAR Inc., Madison, Wis.). Color bar represents gene expression intensity (log 2 scale).
Figure 6A:
FIG. 6A illustrates RV-C15 replication in HeLa cells transfected with CDHR3 cDNA, specifically, genome structure of the RV-C15 infectious clone expressing GFP. Two viral 2A protease cleavage sites permitting the release of GFP after polyprotein translation are indicated.
Figure 6B:
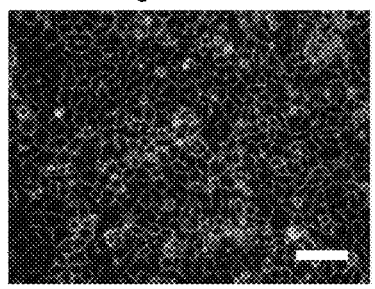
FIG. 6B illustrates RV-C15 replication in HeLa cells transfected with CDHR3 cDNA, specifically, GFP expression 48 h after C15-GFP infection of HeLa cells transfected with wild-type CDHR3 for 48 hours. Scale bar, 100 µm.
Figure 7A:
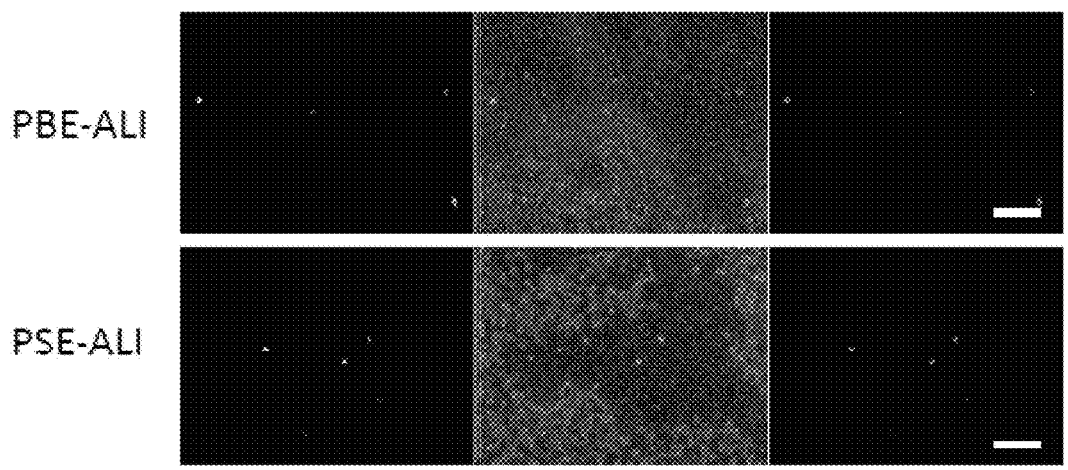
FIG. 7A illustrates RV-C15-GFP infection of ALI cultures of primary human airway epithelial cells, specifically, fluorescent microscopy of differentiated bronchial (PBE) and sinus (PSE) epithelial cells grown at air-liquid interface (ALI) 24 hours after infection with RV-C15-GFP (5×10e6 PFUe per well). Scale bar, 200 µm.
Figure 7B:
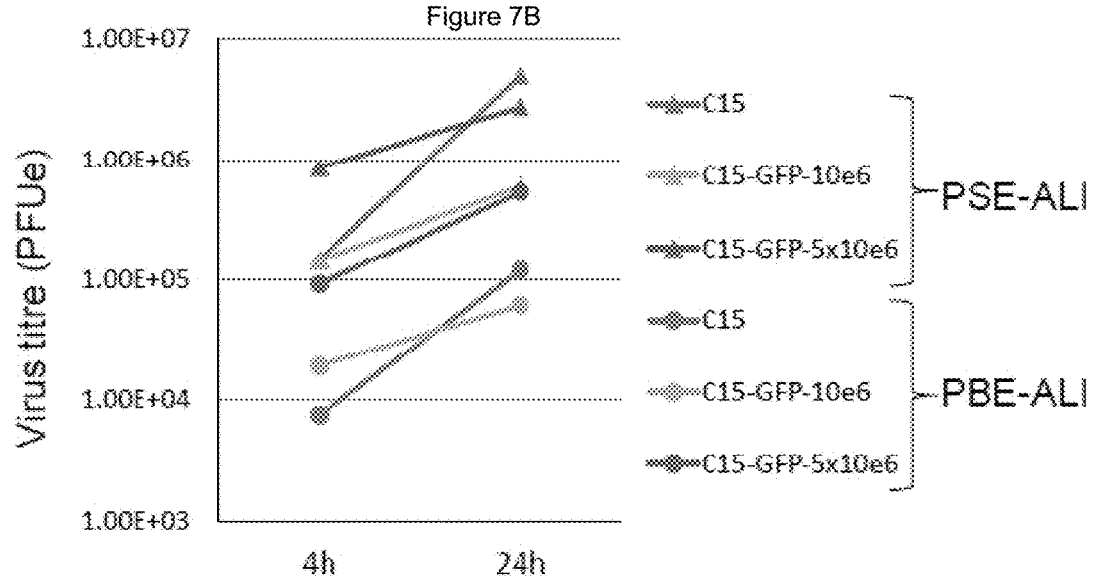
FIG. 7B illustrates RV-C15-GFP infection of ALI cultures of primary human airway epithelial cells, specifically, viral RNA quantification in RVC15 (10e6 PFUe per well) and RV-C15-GFP-infected ALI cultures by qRT-PCR.

We next selected a subset of candidate genes (IL5RA, CCRL1, CDHR3, LDLRAD1, CHDC2, MS4A8B) for functional validation (FIG. 3 and FIG. 5). We transfected HeLa cells with plasmid DNAs encoding the identified genes under control of the CMV promoter. The cells were then exposed to a reporter virus (RV-C15-GFP) engineered to express green fluorescent protein (GFP) during replication (FIG. 6A) to facilitate the analysis. This reporter virus replicated well in susceptible ALI cultures of airway epithelial cells (FIG. 7). We repeatedly detected GFP expression only in cells transfected with CDHR3 cDNA (FIG. 6B).

Figure 6C:
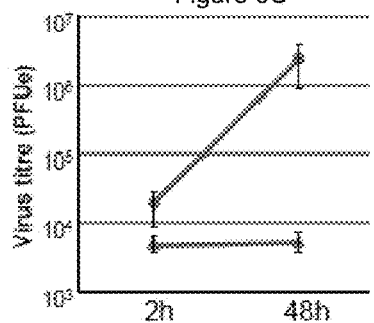
FIG. 6C illustrates RV-C15 replication in HeLa cells transfected with CDHR3 cDNA, specifically, RV-C15 binding (2 h p.i.) and replication (48 h p.i.) in HeLa cells transfected with wild-type CDHR3 (o), or Lipofectamine 2000 control (Δ) for 48 hours (n=5, data are means±SD).

To confirm that this result was not unique to the GFP-expressing virus, we then infected CDHR3-expressing HeLa cells with wild-type RV-C15. Relative to untransfected cells, we again observed enhanced virus binding and evidence of vigorous replication (~2 log increase in RV-C RNA compared to input) (FIG. 6C). Therefore, transfection-induced expression of human cadherin-related family member 3 (CDHR3) was sufficient to convert HeLa cells normally unsusceptible to RV-C infection into targets that supported virus binding and subsequent replication.

Example 2

Mutation in CDHR3 ($Cys_{529} \rightarrow Tyr$) Increases RV-C Binding and Progeny Yields CDHR3 is a member of the cadherin family of transmembrane proteins. Typically, cadherins are involved in homologous cell adhesion processes that are important for epithelial polarity, cell-cell interactions and tissue differentiation. Four alleles of CDHR3 are described, of which one representing a single nucleotide polymorphism (G→A) that converts residue cysteine to tyrosine at position 529 ($Cys_{529} \rightarrow Tyr$, rs6967330), was recently linked with a much greater risk of asthma hospitalizations and severe exacerbations in young children in a genome-wide association study. This point mutation in cadherin-repeat domain 5 near a calcium binding site leads to a marked increase in cell surface expression of the CDHR3 protein, presumably, by altering the protein conformation.

When we engineered this single change into CDHR3 cDNA and then expressed it in HeLa cells, there was higher

TABLE 1

Expression of the known major and minor group rhinovirus receptors in the cell cultures and tissue specimens used in this study.

Figure 6D:
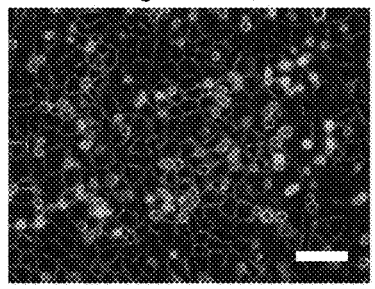
FIG. 6D illustrates RV-C15 replication in HeLa cells transfected with CDHR3 cDNA, specifically, GFP expression 48 h after C15 infection of HeLa cells transfected with CDHR3 $Cys_{529}$→Tyr variant for 48 hours. Scale bar, 100 µm.
Figure 6E:
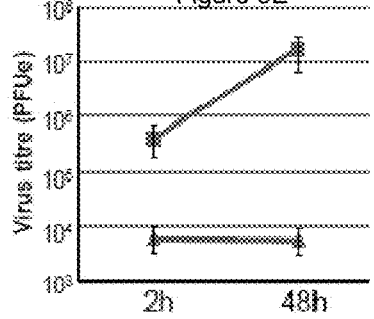
FIG. 6E illustrates RV-C15 replication in HeLa cells transfected with CDHR3 cDNA, specifically, RV-C15 binding (2 h p.i.) and replication (48 h p.i.) in HeLa cells transfected with CDHR3 $Cys_{529}$→Tyr variant (□), or Lipofectamine 2000 control (Δ) for 48 hours (n=3, data are means±SD).
Figure 6F:
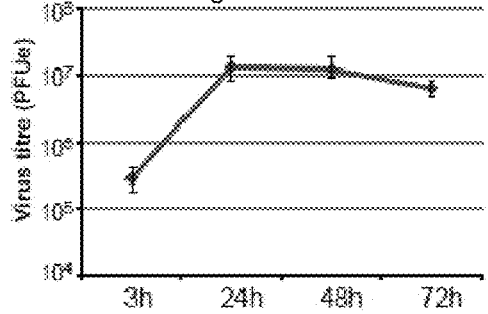
FIG. 6F illustrates RV-C15 replication in HeLa cells transfected with CDHR3 cDNA, specifically, the growth curve of C15 in HeLa cells transfected with CDHR3 $Cys_{529}$→Tyr variant for 48 hours (n=3, data are means±SD).
Figure 8:
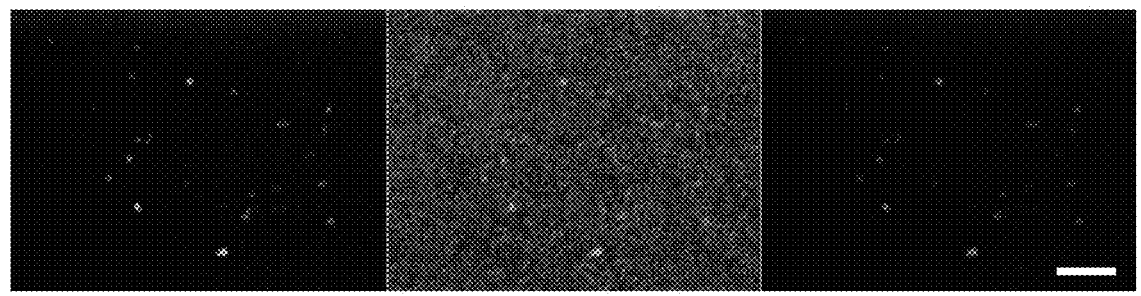
FIG. 8 illustrates RV-C15-GFP infection of HEK293T cells transfected with CDHR3 Cys529→Tyr variant DNA. HEK293T cells were transfected with Cys529→Tyr variant of CDHR3 for 24 hours and infected with RV-C15-GFP at 10e6 PFU per well in 12-well plate for 42 hours. Scale bar, 200 µm.

| | | Mean gene expression (log2 value) | | | | | | |
|---|---|---|---|---|---|---|---|---|
| Probe Set ID | Gene symbol | Sinus monolayer | Sinus ALI | Sinus tissue | Nasal brushing | Sinus suspension | Cell lines | Primary cells |
| 8025601 | ICAM1 | 8.08 | 9.42 | 8.09 | 8.48 | 11.53 | 9.47 | 8.24 |
| 8025828 | LDLR | 12.42 | 12.19 | 9.69 | 10.22 | 11.98 | 11.14 | 12.31 |
| 8154100 | VLDLR | 8.97 | 8.44 | 8.37 | 7.97 | 8.40 | 8.85 | 9.85 |
| 7956301 | LRP1 | 9.60 | 9.55 | 9.96 | 9.61 | 9.27 | 10.29 | 9.85 | level of GFP expression (FIG. 6D) and about 10-fold greater RV-C15 binding and subsequent progeny yield, relative to the wild-type CDHR3 (FIG. 6E). Parallel experiments with another human cell line (HEK293T) again showed that CDHR3 expression conferred susceptibility to RV-C infection (FIG. 8). The phenomenon is not unique to the C15 virus type, because cells transfected with CDHR3 also become permissive to C2 and C41 strains (data not shown). In transfected HeLa monolayers, the virus growth kinetics (FIG. 6F) permitted by CDHR3 $Cys_{529}{\rightarrow}Tyr$ variant was similar or better than that of ALI cultures of sinus epithelial cells.

Example 3

An Extended Model of CDHR3 Structure

Figure 10:
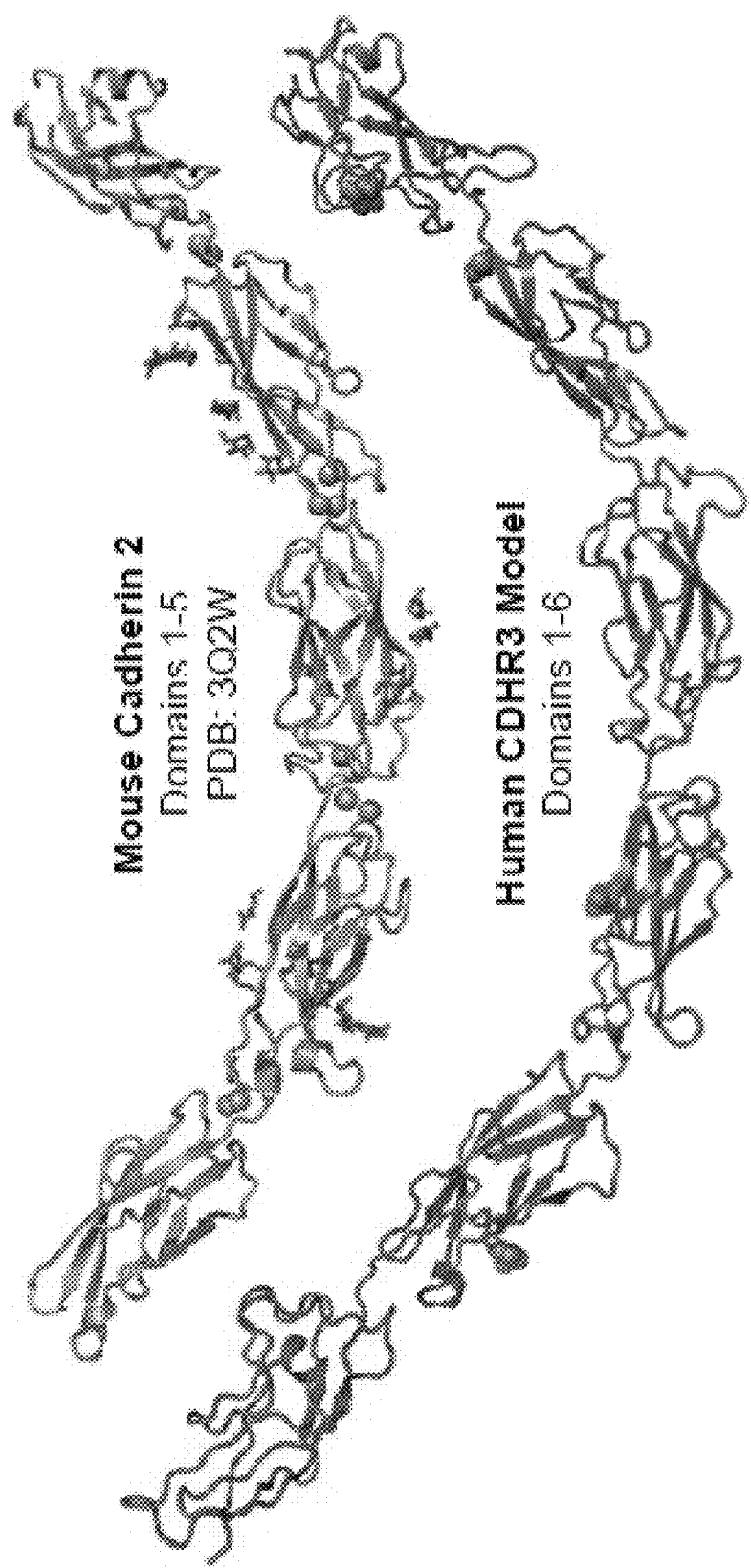
FIG. 10 is a structural model of the complete CDHR3 protein. Structures of the mouse cadherin 2 and human CDHR3 domains 2-5 (model) are published. Domain 1 of CDHR3 (shown in red) was added after I-Tasser modeling relative to known cadherin family protein structures.

The CDHR3 protein sequence (885 aa) has a short signal peptide (19 aa) and 6 tandemly repeated cadherin domains (~100 aa each), followed by transmembrane (63 aa) and C-terminal cytoplasmic (150 aa) domains (FIG. 9A). The structure of CDHR3 has not been determined yet, but an approximation for domains 2-6, as modeled on the mouse N-cadherin ectodomain structure (Protein Data Bank (PDB) code: 3Q2W) is described. We extended this model to include CDHR3 domain 1 (FIG. 10), using I-Tasser and Robetta algorithms to template the domain 1 and 2 sequences on multiple linked-domain cadherin analogs (e.g. PDBs: 1FF5A, 1Q5CA, 2QVIA).

The consensus output was joined to the domains 2-6 model coordinates using the align function of PyMol. Multiple iterations of this process, specifying a range of templates did not alter the general configuration of the final, full-domain structure (average root-mean-square deviation (RMSD): 1.632). The extended model (FIG. 9B) provides predictions of residues displayed on various repeat unit faces including the $Cys_{529}{\rightarrow}Tyr$ mutation at the domain 5-6 junction that defines the "asthmatic" allele.

Example 4

Docking the CDHR3 to a Two-Protomer Model of the RV-C15 Capsid

On cell surfaces or between cells, cadherins self-dimerize through reciprocal domain 1 pairings mediated by cysteine, tryptophan or hydrophobic interactions. There can be multiple glycosylation sites dispersed along the ectodomain. The dimer format of CDHR3 is unknown, but there is a single tryptophan ($Trp_{76}$) residue in domain 1. According to the prediction algorithms, there is also a single putative asparagine-linked glycosylation site ($Asn_{186}$) in domain 2. $Trp_{76}$ and $Asn_{186}$ position as solvent exposed on opposite sides of their respective domains (FIG. 9B). Assuming interactions similar to other picornaviruses, the RV-C viruses are expected to access distal, rather than proximal locations relative to the cellular membrane.

To test the feasibility of virus-receptor interactions, we docked the CDHR3 domains 1, 2 and 3 to a two-protomer model of RV-C15 capsid. Both queried algorithms (Gramm-X and HADDOCK) were given only two constraints: (i) CDHR3 $Asn_{186}$ should be at or near the interface and (ii) the solvent exposed (outer) surface of the capsid proteins should be involved. The preferred complexes docked the receptor across the adjacent protomers, impacting the virus where capsid proteins VP1, 2 and 3 abut, in a 5-fold to 2-fold orientation (FIG. 9C, 9D). In this orientation, $Asn_{186}$ of domain 2 is buried in VP1 contacts and domain 1 extends across the 2-fold with VP1 and VP2 contacts, while domain 3 is free of the virus and $Trp_{86}$ is on a non-docked face (FIG. 9D, 9E).

The RV-C as a species conserves <75% capsid protein identity, but the RV-C15 structure model predicts a single shared receptor. The modeled CHDR3 footprint covers nearly every surface residue of RV-C15 that is conserved within the species (FIG. 3). Moreover, although modeled as a monomer unit, this particular receptor orientation would easily accommodate domain 1 mediated dimer contacts across the 2-fold axis of the virus, or even other multimers around the 5-fold.

Example 5

Mutations in Domains 1 and 2 of CDHR3 Inhibit RV-C Binding

Figure 11A:
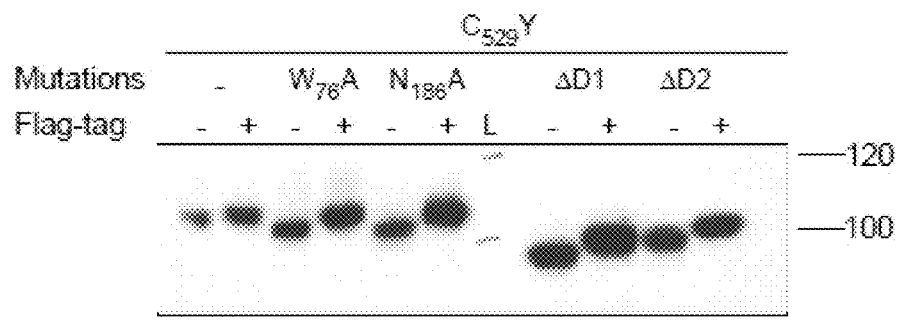
FIG. 11A illustrates the effects of mutations on CDHR3 surface expression and RV-C15 infection, specifically, a western blot analysis of CDHR3 expression in transfected HeLa cells. Cells were transfected with DNA encoding CDHR3 $Cys_{529} \rightarrow Tyr$ variant with or without additional mutations in domains 1 and 2 for 24 hours, lysed and probed with α-CDHR3 polyclonal antibodies. L, protein ladder.

To test the docking model, we either deleted domains 1 or 2, or mutated two important amino acids, $Trp_{76}$ and $Asn_{186}$, predicted to be exposed on the surface of these domains, to alanine, in CDHR3 $Cys_{529}{\rightarrow}Tyr$ variant expressing vector (FIG. 9A). The recombinant FLAG tag sequence (DYKDDDDK—SEQ ID NO:1) was inserted between the signal sequence and domain 1 to facilitate detection of CDHR3 surface expression (FIG. 9A). This tag did not affect virus binding or replication (data not shown). Western blot analysis showed that all mutants are expressed equally well in transfected HeLa cells (FIG. 11A); however, the cellular localization of the proteins was different. Deletions of domains 1 or 2 almost completely abolished surface expression of CDHR3 mutants whereas point mutations had little or no effect (FIG. 11B).

Figure 11B:
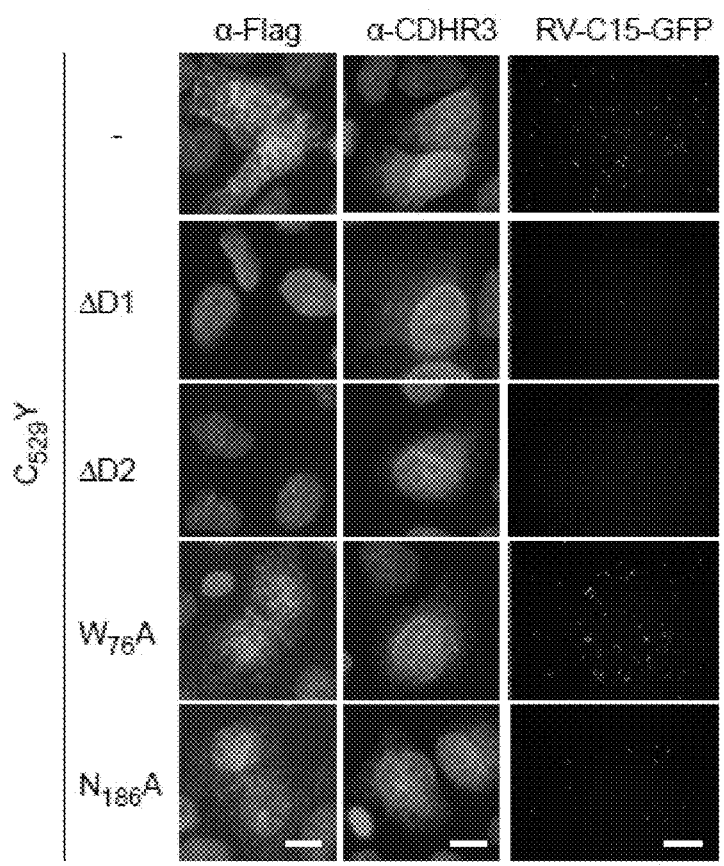
FIG. 11B illustrates the effects of mutations on CDHR3 surface expression and RV-C15 infection, specifically, confocal (two left panels) or wide-field (right panel) fluorescent microscopy images of cells transfected as in panel (a) and either fixed with 4% paraformaldehyde to visualize CDHR3 cellular localization or infected with RV-C15-GFP for 48 h. Permeabilized (α-CDHR3) or non-permeabilized (α-FLAG) HeLa cells were stained with the corresponding antibodies to visualize intracellular or surface expression, respectively. Scale bars, 10 μm (confocal) and 200 μm (wide-field fluorescent).
Figure 11C:
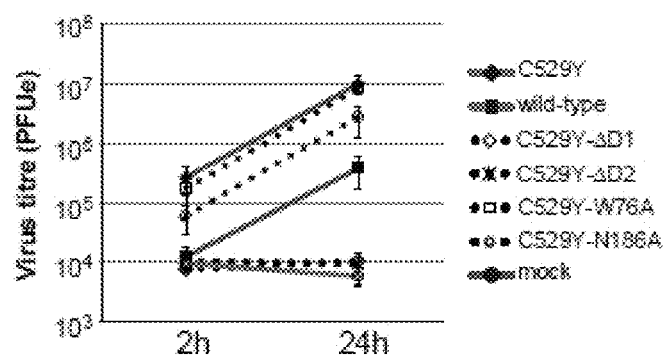
FIG. 11C illustrates the effects of mutations on CDHR3 surface expression and RV-C15 infection, specifically, the RV-C15 binding (2 h p.i.) and replication (24 h p.i.) in HeLa cells transfected with CDHR3 $Cys_{529} \rightarrow Tyr$ variant with or without additional mutations in domains 1 and 2, or Lipofectamine 2000 control (mock) for 24 hours (n=3, data are means±SD).

Infection of the transfected cells with wild-type or reporter RV-C15 showed that both deletions eliminated virus binding and replication in accordance with the intracellular localization of mutated proteins (FIG. 11B,C). Interestingly, while point mutation of $Asn_{186}{\rightarrow}Ala$, a putative glycosylation site in domain 2, preserved surface expression, it significantly (more than 70%) impaired virus binding and subsequent replication. These findings confirm the predicted importance of domain 2 for binding to RV-C15.

Example 6

Methods of Transducing the HeLa Cell Line into Expressing CDHR3 $C_{529}Y$ Variant In this example, we show the viral vectors useful for transduction of the RV-C virus into cell lines previously unsusceptible to growth of the RV-C.

By "transduction" we mean the introduction of foreign DNA into another cell via a viral vector.

By "viral vector" we mean any viral-based tool (e.g. retrovirus or adenovirus) used to safely deliver genetic material into cells. Common examples of viral vectors include retro/lentiviruses such as, for example, pDuet011, pNG72, pLX304 and others known to the art as well as adenoviral vectors known to the art.

By "pDuet011" we mean the HIV-based vector with human UBC promoter to express gene of interest. In use, the pDuet011 vector provided a low level expression of CDHR3.

By "pNG72" we mean the murine leukemia virus (MLV) based vector utilizing MLV promoter to express gene of interest. In use, pNG72 provided a medium-to-high level expression of CDHR3 and the resultant transduced cells were susceptible to RV-C infection. However, the virus progeny yields were suboptimal. Cells were grown two passages after transduction and selected using G418 antibiotic. Polyclonal cells (~10e7) were frozen without clonal selection.

By "pLX304" we mean the HIV-based vector utilizing robust CMV promoter to express gene of interest. In use, the pLX304 vector provides a high level expression of CDHR3, and the resultant transduced cells should be susceptible to RV-C infection. The vectors are publicly available, as known by those of skill in the art. For example, pLX304 expressing wild-type CDHR3 was purchased from TransOmic. pDuet011 and pLX304 lentiviral vectors are also available for purchase from Addgene for a small fee. pNG72 was provided by Dr. Nate Sherer (UW-Madison).

We currently produce RV-C by transfection of RNA synthesized in vitro from a linearized cDNA copy of the viral genome. High-throughput large-scale propagation of RV-C by infection of HeLa cells stably expressing the CDHR3-$C_{529}Y$ variant will enable production of large quantities of virus similarly to other RV species.

The optimal way of large-scale rhinovirus production is infection of HeLa cells in suspension culture. This culture utilizes growth medium lacking calcium which is necessary for cadherins to function properly. Calcium serves to rigidify the cadherin extracellular domains and promote trans junctional interactions. Alternatively, transduced HeLa cells can be grown as monolayers. Expected virus yields should be ≥$10^8$ PFUs per T75 flask of cells.

These cells can also be used to develop RV-C infectivity assays (e.g. plaque or $TCID_{50}$) for antiviral drug screening, or for detection of neutralizing antibody response to RV-C in clinical studies.

The large quantities of highly-purified RV-C are necessary to determine the virion crystal structure, for RV vaccine development, and the transduced cell line can be used, for example, to study mechanisms of virus spread and to define RV-C molecular virology in basic research studies.

Example 7

Methods & Materials

Cell cultures. Sinus epithelial tissue samples were obtained from residual surgical specimens from individuals undergoing sinus surgery and cultured as described previously (See Bochkov, Y. A. et al. Nat. Med., 2011, 17, 627-632). The protocol was approved by the University of Wisconsin-Madison Human Subjects Committee. To isolate primary epithelial cells, the tissue was washed with PBS and digested by pronase (Roche) and DNase (Sigma). Primary airway epithelial cells were cultured submerged (undifferentiated monolayers) or at air-liquid interface (fully-differentiated) as previously described. HeLa (ATCC# CRL-1958) and WisL (human embryonic lung fibroblast) cells were grown in Eagle's Minimum Essential Medium (Lonza); HEK293T (ATCC# CRL-11268) and NCI-H358 (ATCC# CRL-5807) cells were cultured in Dulbecco's Modified Eagle's Medium (Cellgro). Both culture media were supplemented by non-essential amino acids (Gibco) and 10% fetal bovine serum.

Viruses and infection. Recombinant RV-C15 and RV-C15-GFP were produced by transfecting viral RNA synthesized in vitro from linearized infectious cDNA clones into WisL cells as previously described. After three freeze and thaw cycles, the transfected cell lysates were clarified by low-speed centrifugation, treated with RNase A (10 µg/ml, Qiagen) to destroy input RNA, purified by pelleting through a 30% sucrose cushion (200,000×g, 10° C., 2 hours) and resuspended in PBS. Cells grown in 12-well plates (monolayers) or in Transwell polycarbonate inserts (0.4 µm pore size, Corning) (ALI cultures) were inoculated with RV-C15 or RV-C15-GFP at $10^6$ PFUs per well or insert, incubated for 2-4 hours at 34° C., and washed 3 times with PBS to remove unattached input virus. Infected cells were lysed 24-72 hours after infection using RLT buffer (Qiagen) and stored at −80° C.

RNA extraction and quantitative (q) RT-PCR. Total RNA was extracted from sinus tissue or cultured cells using the RNeasy™ Mini kit (Qiagen). Viral RNA concentrations were determined by qRT-PCR using Power SYBR Green™ PCR mix (Applied Biosystems) as previously described, and normalized to human β-actin (ACTB) expression (#4326315E, Applied Biosystems) in infected cells.

Construction of the pC15-GFP infectious clone. The full-length infectious clone of RV-C15 was published (See Bochkov, Y. A. et al. Nat. Med., 2011, 17, 627-632). We amplified the enhanced (e) GFP and C15 2A protease fusion sequence from the pcDNA3-GFP and pC15-Rz cDNA templates by two-step PCR procedure using the flanking primers 2A-GFP-1f and C15-SacI-r and internal primers GFP-2A-2r and GFP-2A-3f (Table 2). The resulting amplicon (1116 base pairs) was digested by BlpI and BstAPI and cloned into pC15 to generate pC15-GFP. The eGFP sequence was inserted in frame between VP1 and 2A protease and flanked by two 2A protease recognition sites (LISSA/GPS) to release the GFP from viral polyprotein upon translation.

Expression plasmids and transfection. Plasmids for expression of receptor candidate genes CCRL1 (Missouri S&T cDNA Resource Center), MS4A8 (OriGene), CHDC2 and CDHR3 (TransOmic) were purchased. IL5RA and LDL-RAD1 ORFs were PCR amplified from a cDNA sample obtained from differentiated airway epithelial cells using the corresponding primers (all of the primers used for cloning are listed in Table 2). The resulting amplicons were cloned into pIRES plasmid (Clontech) using restriction enzyme sites XhoI and XmaI to express the genes of interest under control of the CMV promoter. Mutation in domain 5 ($C_{529}Y$) of CDHR3 was engineered by two-step PCR using the flanking (CDHR3-f3 and CDHR3-r3) and internal (CDHR3-0529Y-f and CDHR3-0529Y-r) primers and restriction sites SacI and Bsu36I in pCDHR3. The resulting construct was designated pCDHR3-$C_{529}Y$. To create pCDHR3-FLAG-$C_{529}Y$, the FLAG tag sequence (DYKDDDDK—SEQ ID NO:1) was inserted between the signal sequence and domain one (as described in ref. 19) using flanking (CDHR3-f4 and CDHR3-r4) and internal (CDHR3-FLAG-f and CDHR3-FLAG-r) PCR primers and MfeI and SacI restriction sites in pCDHR3-$C_{529}Y$. Mutations in domains 1 and 2 of CDHR3 were created by two-step PCR using indicated internal primer pairs (Table 2) and flanking primers CDHR3-f and CDHR3-r. pCDHR3-$C_{529}Y$ or pCDHR3-FLAG-$C_{529}Y$ plasmids were used as templates. Following PCR, the mutant amplicons were digested with restriction enzymes AleI and BsrGI and ligated into the pCDHR3-$C_{529}Y$ vector cut with the same restriction enzymes. The transfection-grade plasmid DNAs was prepared by Plasmid Maxi™ kit (Qiagen) and transfected into monolayers of HeLa or HEK293T cells using Lipofectamine 2000™ (Life Technologies) according to the manufacturer's instructions.

TABLE 2

Primers used for construction of GFP-expressing RV-C15 infectious clone, expression plasmids and site-directed mutagenesis of CDHR3.

| Primer | Sequence(5'-3') |
|---|---|
| 2A-GFP-1f | CATCAGCTCAGCTGGACCTAGTGTGAGCAAGGGCGAGGAGCT SEQ ID NO: 2 |
| GFP-2A-2r | GTCCCGCAGAACTGATGAGCTTGTACAGCTCGTCCATGCCGA SEQ ID NO: 3 |
| GFP-2A-3f | ACAAGCTCATCAGTTCTGCGGGACCGAGCGACATGTTTGTGC SEQ ID NO: 4 |
| C15-SacI-r | CCTGCAGTGATCATACCAATCACA SEQ ID NO: 5 |
| IL5RA-f | ATCACTCGAGATGATCATCGTGGCGCATGTAT SEQ ID NO: 6 |
| IL5RA-r | TGATCCCGGGTCAAAACACAGAATCCTCCAGG SEQ ID NO: 7 |
| LDLRAD1-f | ATCACTCGAGATGAACAAGGTCTTCCCCCA SEQ ID NO: 8 |
| LDLRAD1-r | TGATCCCGGGTCAGGGTCCGGGACAGG SEQ ID NO: 9 |
| CDHR3-f3 | TCATCGTGGAGGTGAGGGACAG SEQ ID NO: 10 |
| CDHR3-C529Y-f | TAAAGTGGACTATGAAACAACCCCCATCTA SEQ ID NO: 11 |
| CDHR3-C529Y-r | TAGATGGGGGTTGTTTCATAGTCCACTTTA SEQ ID NO: 12 |
| CDHR3-r3 | CGGCACGTACCATGCAGATG SEQ ID NO: 13 |
| CDHR3-f4 | CCAGTATCTGCTCCCTGCTTGTGT SEQ ID NO: 14 |
| CDHR3-FLAG-r | GATTAGGTGTAGCTTATCGTCGTCATCCTTGTAATCTGCTTCTC CCCCTGACATG SEQ ID NO: 15 |
| CDHR3-FLAG-f | GAGAAGCAGATTACAAGGATGACGACGATAAGCTACACCTAA TCCTCTTACCTGCTA SEQ ID NO: 16 |
| CDHR3-r4 | GGACTCAGTTCCTCCAGGACTGTGT SEQ ID NO: 17 |
| CDHR3-W76A-f | GCTTTTAGGGTGAATGCGCTGTCAGGCACCTAC SEQ ID NO: 18 |
| CDHR3-W76A-r | GTAGGTGCCTGACAGCGCATTCACCCTAAAAGC SEQ ID NO: 19 |
| CDHR3-N186A-f | CAGAATGTCTGCTGCTGGCACCCTCTTCTC SEQ ID NO: 20 |
| CDHR3-N186A-r | GAGAAGAGGGTGCCAGCAGCAGACATTCTG SEQ ID NO: 21 |
| CDHR3-N186Q-f | CAGAATGTCTGCTCAAGGCACCCTCTTCTC SEQ ID NO: 22 |
| CDHR3-N186Q-f | GAGAAGAGGGTGCCTTGAGCAGACATTCTG SEQ ID NO: 23 |
| CDHR3-ΔD1-r | TAGAGGTGGAGGGGATTTGAGTTGACTATCTG SEQ ID NO: 24 |
| CDHR3-ΔD1-f | ATCCCCTCCACCTCTACATAGTAGAAAGAGCAAACC SEQ ID NO: 25 |
| CDHR3-ΔD2-r | TCGTTGAGGTGTAGACCTTCTGCCAAGTTGCCTTGAAACTGAG G SEQ ID NO: 26 |
| CDHR3-ΔD2-f | TCTACACCTCAACGACGAAGTCCCTCGCTTTACCAGCCCGAC SEQ ID NO: 27 |
| CDHR3-f | GTAGGCGTGTACGGTGGGAG SEQ ID NO: 28 |
| CDHR3-r | CTCCAGGACTGTGTACACTCGTGTC SEQ ID NO: 29 |

Confocal and wide-field fluorescent microscopy. HeLa cells plated on glass coverslips were transfected with 1 µg of pCDHR3 DNA using Lipofectamine 2000 (Life Technologies). 24 hours post-transfection cells were fixed with 4% paraformaldehyde for 5 min at 25° C. For detection of total cellular CDHR3 expression, cells were permeabilized (15 min, 25° C.) with PBST (PBS containing 0.2% Triton, 0.5% Tween) before washing with PBS and blocking with 10% NBS and 10% BSA for 1 hour at 25° C. For detection of cell surface expression of CDHR3, non-permeabilized fixed cells were washed (2×) with PBS and then blocked with 10% NBS and 10% BSA for 1 hour at 25° C. After washing (3× with PBS), cells were reacted with primary antibody in 1% BSA in PBS solution overnight at 4° C.

The permeabilized cells were stained with rabbit polyclonal anti-CDHR3 (Sigma, HPA011218) and the non-permeabilized cells were stained with rabbit monoclonal anti-FLAG (Sigma, F2555) antibodies. The cells were then washed (3×) with PBS and treated with DAPI and anti-rabbit Alexa Fluor-594 antibodies (Life Technologies, A-11012) in 2% BSA in PBS solution for 1 hour at 25° C. Staining of the CDHR3 protein in transfected cells was visualized on a Nikon ECLIPSE Ti80 confocal microscope. Live cell imaging of GFP-expressing cells infected with RV-C15-GFP was done on an Olympus IX71 inverted fluorescent microscope.

Western Blot. HeLa cells transfected with 1 µg of pCDHR3 DNAs per well in 12-well plates were lysed 24 hours post-transfection in 2×SDS gel loading buffer and boiled. Proteins were fractionated by SDS-PAGE and then electrotransferred onto PVDF membranes (Immobilon-P; Millipore). The membranes were blocked with Tris-buffered saline-Tween 20 (TBS-T: 20 mM Tris pH 7.6, 140 mM NaCl, 0.5% Tween-20) containing 10% nonfat dry milk and then washed (3×) with TBS-T before incubation with rabbit polyclonal anti-CDHR3 (Sigma, HPA011218) in TBS-T with 1% nonfat dry milk over night at 4° C. The membranes were then washed again (3×) with TBS-T before incubation with horseradish peroxidase-conjugated anti-rabbit IgG, (Promega, W401) in TBS-T with 1% nonfat dry milk. After final washes, the membranes were exposed to film in the presence of enhanced chemiluminescence substrate (Pierce, 32106).

It should be noted that the above and below description, attached figures and their descriptions are intended to be illustrative and not limiting of this invention. Many themes and variations of this invention will be suggested to one skilled in this art and, in light of the disclosure. All such themes and variations are within the contemplation hereof. For instance, while this invention has been described in conjunction with the various exemplary embodiments outlined above, various alternatives, modifications, variations, improvements, and/or substantial equivalents, whether known or that are or may be presently unforeseen, may become apparent to those having at least ordinary skill in the art. Various changes may be made without departing from the spirit and scope of the invention. Therefore, the invention is intended to embrace all known or later-developed alternatives, modifications, variations, improvements, and/or substantial equivalents of these exemplary embodiments.

Example 8

Adapted Rhinovirus C

Rhinovirus C species (RV-C) was discovered in 2006 and is of special interest because RV-C isolates can cause more severe illnesses in children compared to other rhinoviruses and are closely associated with asthma exacerbations. As described above, we developed the first culture systems for RV-C (sinus mucosal organ culture and air-liquid interface (ALI) culture of differentiated airway epithelial cells), the first virus production methods (reverse genetics from viral RNA synthesized in vitro) and discovered that human cadherin-related family member 3 (CDHR3) protein mediates virus binding and replication.

As described above, we have also developed (by lentivirus transduction) a HeLa cell line (HeLa-E8) stably expressing the mutated CDHR3 sequence ($C_{529}Y$) with increased cell surface localization of the variant protein that supports propagation of RV-C by infection.

We became interested in developing a rhinovirus C strain that has a more robust propagation potential in HeLa-E8 expressing the mutated CDHR3 sequence compared to clinical isolates.

In one aspect, the present invention is an adaptation of a RV-C15 clinical isolate for optimal propagation in a transduced HeLa-E8 cell line expressing CDHR3. In one embodiment of the present invention, the rhinovirus C isolate has the following mutations: $T_{125}K$ in VP1 and $E_{41}K$ in 3A. The preferred HeLa cell line adapted C15 virus strain (RV-C15a, described below) of the present invention induces strong cytopathic effect and replicates vigorously in the HeLa-E8 cells, yielding more than a log higher level of infectious rhinovirus particles compared to that of parental clinical isolate. This adapted virus can be used for large-scale cost-effective production of RV-C by infection and for testing antiviral compounds by infectivity assays (such as virus plaque assay) or utilizing reporter-expressing RV-C15a.

The RV-C15 clinical isolate replicates well (more than 2-log increase in viral RNA from 2 h to 24 h post infection) in HeLa-E8 cells but induces very mild cytopathic effect (CPE) in this cell line. However, RV-C15 progeny yields after infection are still about 1-log lower compared to a HeLa-adapted isolate of RV-A16 type. We wished to develop an adaptation of RV-C15 that would maximize replication levels and virus yields when infected in cultured HeLa-E8 cells.

Referring to FIG. 13, HeLa-E8 cells, cultured in a 12-well plate, were infected with recombinant RV-C15 at multiplicity of infection (MOI) of 10 plaque forming unit equivalents (PFUe) per cell. Infected cells were collected 72 h post infection (p.i.) and lysed by three freeze-thaw (−80° C./25° C.) cycles to release virus particles from cells. Virus-containing cell lysates were clarified by centrifugation at 10,000×g (10 min, 4° C.) and used for the next round of infection (passage 2 [P2]). The virus was serially passaged a total of 9 times in a 12-well plate format and then the culture was scaled up to a 6-well plate (P10) and T75 flask (P11).

Serial passaging of RV-C15 resulted in CPE progression starting from moderate (~10% rounded and detached cells) at P5 to severe (≥50%) effects at passage 10 and higher. (Cytopathic effect or cytopathogenic effect, abbreviated CPE, refers to structural changes in the host cells that are caused by viral invasion)

The seed virus after passage 11 was used for infection of twelve T75 flasks (P12) and virus purification. Viral RNA was extracted from RV-C15-P10, reverse transcribed with both oligo(dT) and random hexamers, and amplified by PCR using C15 specific primers. PCR products (n=10) were cloned in pGEM-T Easy vector (Promega) and sequenced (≥6× coverage). Assembled complete genome sequence of HeLa-E8 adapted RV-C15 (RV-C15a) was compared to that of parental RV-C15 isolate (RV-C15-wild type).

Sequence analysis revealed several missense mutations found in both the structural (VP3 and VP1) and nonstructural (3A) proteins of RV-C15a.

These mutations were introduced individually or in combination into the RV-C15 cDNA for recombinant virus production and virus binding and replication tests. The analysis has shown that adaptation is acquired by only two key mutations responsible for increased binding ($T_{125}K$ in VP1) and replication ($E_{41}K$ in 3A) in HeLa-E8, respectively. The mutation numbering is consistent with residue numbering found in the following publication: Y. A. Bochkov, A. C. Palmenberg, W. M. Lee, J. A. Rathe, S. P. Amineva, X Sun, T. R. Pasic, N. N. Jarjour, S. B. Liggett, J. E. Gern, *Molecular modeling, organ culture and reverse genetics for a newly identified human rhinovirus C, Nat. Med.* 17 (2011) 627-632. Sequence analysis of VP1 and 3A from other RV-C types (clinical isolates) revealed that both $T_{125}$ and $E_{41}$ represent the dominant residues at this position (48% and 84% of isolates, respectively).

Amino-acid residues are numbered from the amino-terminus of each individual viral protein, including position 125 in VP1 and position 41 in the 3A protein according to a system commonly used for picornaviruses. The GenBank accession number of RV-C15 complete genome sequence is GU219984 and the corresponding polyprotein accession number is ACZ67658. Although the full-length polyprotein residues are consecutively numbered from 1 to 2153 in the GenBank entry, the mutated residues can still be easily found in the published sequence that has individual protein locations in the Features. The mutated residue positions are $T_{692}K$ in VP1 and $E_{1454}K$ in 3A when using consecutive numbering from the amino-terminus of the whole polyprotein.

The rhinoviral genome consists of 3 coding regions designated P1, P2 and P3. The P1 region encodes the structural (or capsid) proteins whereas the P2 and P3 regions encode the nonstructural proteins associated with replication. There are four genes in P1 (1A, 1B, 1C and 1D) that encode four capsid proteins VP4, VP2, VP3 and VP1, respectively. Therefore, the VP1 protein is encoded by the 1D gene. As for the nonstructural proteins, gene and protein names are the same so the 3A protein is encoded by the 3A gene. FIG. 13 depicts the viral genome and contains the gene designations.

Figure 14:
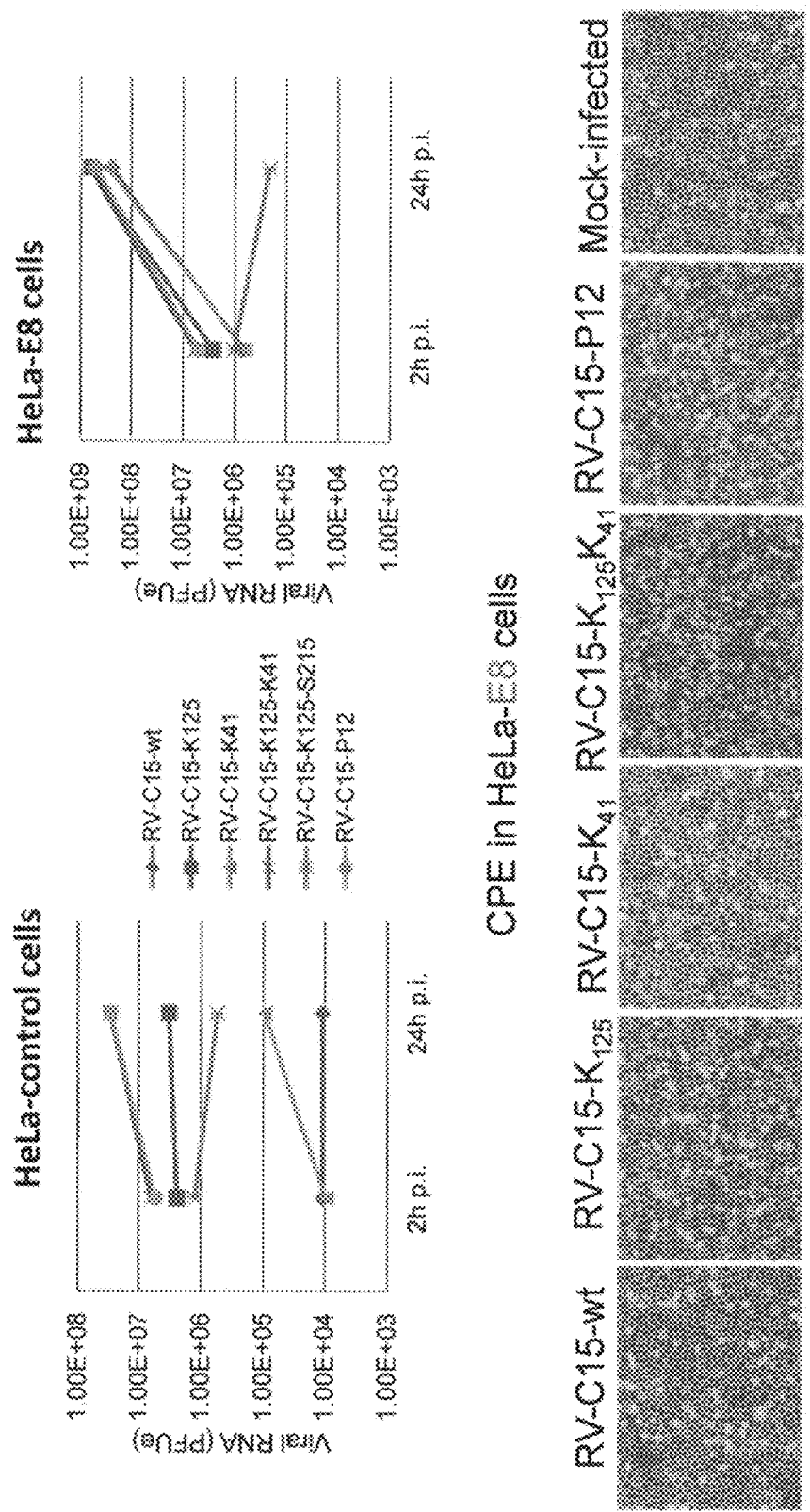
FIG. 14 shows RV-C15 binding and replication in HeLa cells. Control (parental) or transduced (HeLa-E8) cells were infected with RV-C15 samples for 24 hours. Viral RNA was quantitated at 2 h (binding) and 24 h (replication) post infection by real-time PCR.

Referring to FIG. 14, binding and progeny yields of RV-C15a after infection of HeLa-E8 were more than a log higher compared to that of RV-C15-wt. Surprisingly, RV-C15a binds both control and transduced (E8) HeLa cells to similar levels. However, virus replication in HeLa-E8 cells expressing CDHR3 is about 2 orders of magnitude higher compared to control cells. RV-C15a replicates slightly less efficiently in natural host cells (ALI cultures of airway epithelial cells) than RV-C15-wt in agreement with adaptation to a different cell type (HeLa).

Figure 15:
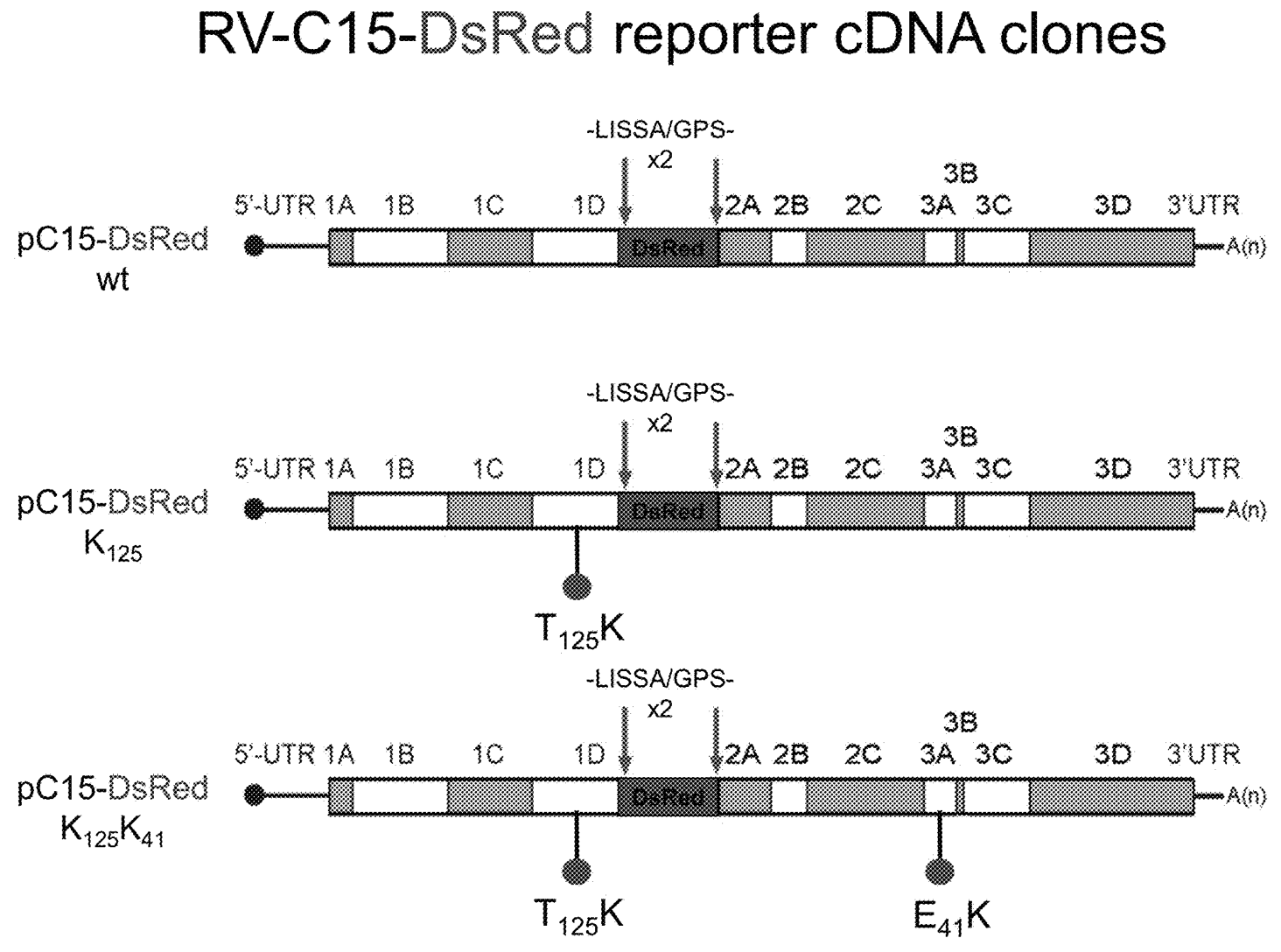
Figure 16:
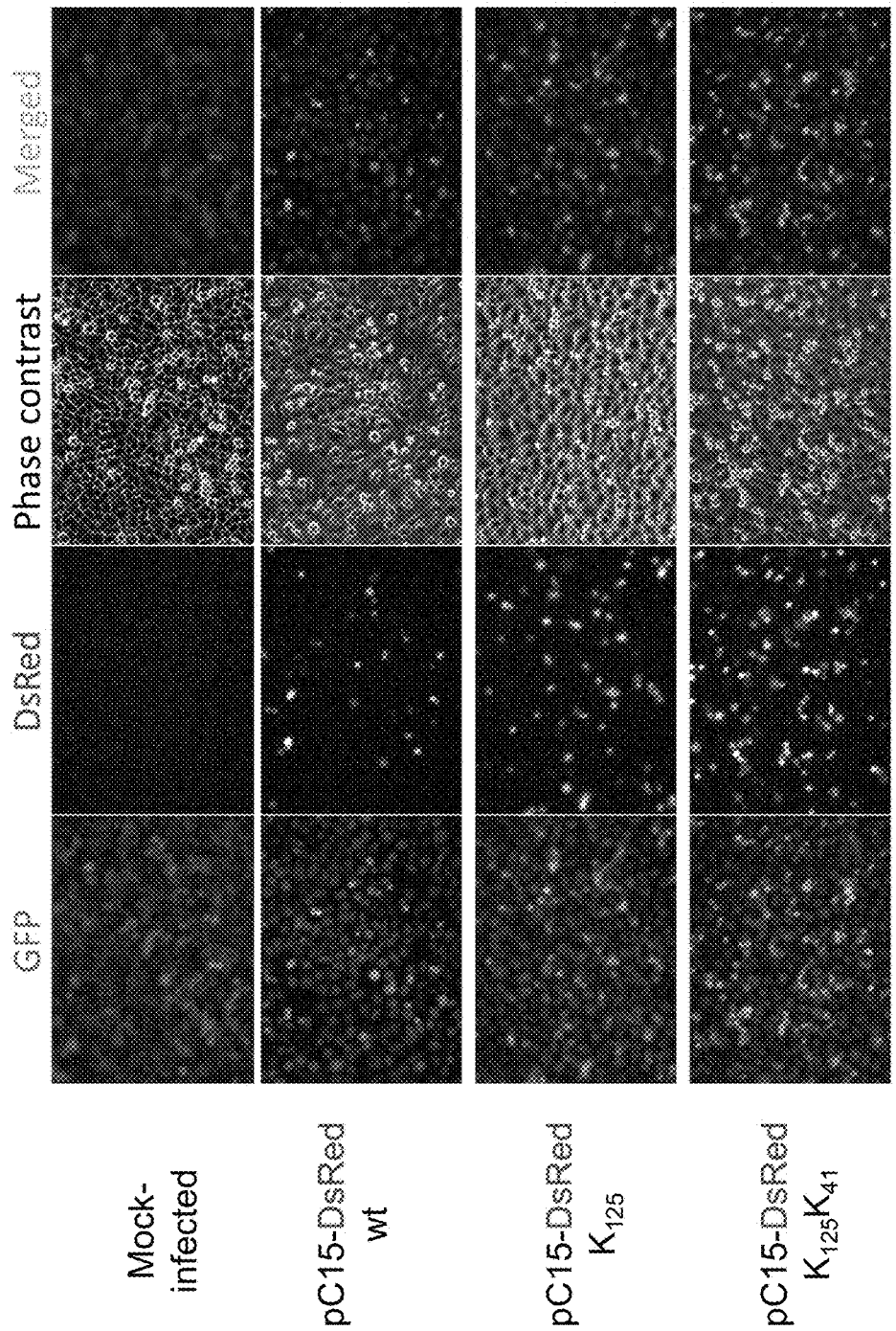
FIG. 16 shows RV-C15-DsRed replication in HeLa-E8 cells. Fluorescent microscopy imaging of HeLa-E8 cells infected with RV-C15 reporter viruses for 48 h.

Referring to FIGS. 15-17, we also constructed the RV-C15-DsRed infectious clone expressing DsRed reporter after virus infection, introduced $T_{125}K$ and $E_{41}K$ mutations and compared the construct with wild-type RV-C15-DsRed reporter virus. Fluorescent microscopy confirmed increased replication, virus spread in culture and CPE progression from 24 to 72 h p.i. of RV-C15-DsRed-$K_{125}/K_{41}$ compared to the wild-type reporter virus.

Referring to FIGS. 15-17, HeLa-E8 cells (FIG. 16) are transduced cells stably expressing mutated CDHR3 protein whereas HeLa control cells (FIG. 17) are the parental cell line H1-HeLa (ATCC CRL1958).

The two key mutations found in both the structural and nonstructural proteins and responsible for the adapted phenotype can potentially be used for adaptation of other cloned RV-C types by mutating the RV-C virus with the mutations discussed above.

One can simply engineer similar mutations in other available RV-C infectious cDNAs (e.g. RV-C2 and RV-C41) and test the mutated virus binding and replication in HeLa cells.

In summary, we adapted the RV-C15 clinical isolate to increase replication in a transduced HeLa-E8 cell line expressing CDHR3. This adaptation resulted in severe CPE and increased virus binding and replication (≥10-fold) in Hela-E8 monolayers and slightly decreased replication in differentiated airway epithelial cells. We found two key mutations in the VP1 and 3A proteins responsible for HeLa-E8 adapted virus phenotype.

---

We claim:

1. A method of propagating rhinovirus C or rhinovirus C variant, the method comprising the steps of:
   a. obtaining a host cell comprising at least one heterologous CDHR3 receptor; and
   b. infecting the host cell with a sample of rhinovirus C or rhinovirus C variant;
   wherein the rhinovirus C propagates.

2. The method of claim 1 wherein the CDHR3 receptor is a CDHR3-$C_{529}Y$ variant.

3. The method of claim 1 wherein the host cell is a cell able to support rhinovirus C replication.

4. The method of claim 3 wherein the host cell is selected from the group consisting of NCI-H358, WI-38, WisL, HEK293T, BEAS-2B, A549 and HeLa.

5. The method of claim 1 wherein the CDHR3 receptor sequence is transduced into the host cell by a viral vector.

6. The method of claim 1 wherein the CDHR3 receptor sequence is transfected into the host cell by lipofection.

7. The method of claim 1, wherein a viral titer of at least >10e8 PFU equivalents per 10e7 cells grown in monolayer is obtained.

* * * * *

UNITED STATES PATENT AND TRADEMARK OFFICE
CERTIFICATE OF CORRECTION

PATENT NO. : 9,938,507 B2  
APPLICATION NO. : 14/836327  
DATED : April 10, 2018  
INVENTOR(S) : James E. Gern et al.

Page 1 of 1

It is certified that error appears in the above-identified patent and that said Letters Patent is hereby corrected as shown below:

In the Specification

Column 3, Line 32, "Benjamin" should be --Benjamini--.

Column 14, Line 47, "0529Y-f and CDHR3-0529Y" should be --C529Y-f and CDHR3-C529Y--.

Signed and Sealed this  
Fifteenth Day of May, 2018

Andrei Iancu  
*Director of the United States Patent and Trademark Office*